United States Patent
Kovach et al.

(10) Patent No.: US 12,427,046 B2
(45) Date of Patent: Sep. 30, 2025

(54) CONTROLLED ENDOPROSTHESIS BALLOON EXPANSION

(71) Applicant: W. L. Gore & Associates, Inc., Newark, DE (US)

(72) Inventors: Larry J. Kovach, Flagstaff, AZ (US); Joseph B. Koenig, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 18/244,735

(22) Filed: Sep. 11, 2023

(65) Prior Publication Data
US 2024/0074884 A1 Mar. 7, 2024

Related U.S. Application Data

(63) Continuation of application No. 16/783,520, filed on Feb. 6, 2020, now Pat. No. 11,779,481, which is a
(Continued)

(51) Int. Cl.
*A61F 2/958* (2013.01)
*A61F 2/07* (2013.01)
(Continued)

(52) U.S. Cl.
CPC ............. *A61F 2/958* (2013.01); *A61F 2/07* (2013.01); *A61F 2002/072* (2013.01);
(Continued)

(58) Field of Classification Search
CPC ............ A61F 2/958; A61F 2002/9583; A61M 25/1027
See application file for complete search history.

(56) References Cited

U.S. PATENT DOCUMENTS

| 4,503,569 A | 3/1985 | Dotter |
| 4,655,771 A | 4/1987 | Wallsten |

(Continued)

FOREIGN PATENT DOCUMENTS

| CN | 101636130 A | 1/2010 |
| CN | 101822868 A | 9/2010 |

(Continued)

OTHER PUBLICATIONS

International Search Report and Written Opinion issued in PCT/US2016/039565, dated Oct. 10, 2016, 20 pages.
(Continued)

*Primary Examiner* — Sarah W Aleman

(57) ABSTRACT

A medical assembly includes a balloon expandable endoprosthesis comprising a plurality of ringed stent elements flexibly connected to each other via at least one flexible connector, the endoprosthesis being deployable from an undeployed state with an undeployed diameter to a deployed state with a deployed diameter. The medical assembly further includes a catheter assembly comprising a balloon, and a cover along the balloon. The endoprosthesis is coaxially located about the balloon and the cover. One or more portions of the balloon and the cover reach an intermediate diameter between the undeployed diameter and the deployed diameter in which the portions of the balloon and the cover are inflated by increasing an inflation pressure within the balloon and approximately maintained at about the intermediate diameter until the inflation pressure increases by at least 1 atmosphere to overcome a yield strength of the cover.

20 Claims, 10 Drawing Sheets

Related U.S. Application Data continuation of application No. 15/164,657, filed on May 25, 2016, now Pat. No. 10,568,752.

(51) Int. Cl.
- A61F 2/89 (2013.01)
- A61F 2/915 (2013.01)
- A61M 25/10 (2013.01)

(52) U.S. Cl.
CPC ............ *A61F 2/89* (2013.01); *A61F 2/915* (2013.01); *A61F 2250/0018* (2013.01); *A61M 2025/1004* (2013.01); *A61M 2025/1059* (2013.01); *A61M 2025/1081* (2013.01); *A61M 2025/1084* (2013.01)

(56) References Cited

U.S. PATENT DOCUMENTS

| | | |
|---|---|---|
| 4,739,762 A | 4/1988 | Palmaz |
| 4,776,337 A | 10/1988 | Palmaz |
| 4,884,573 A | 12/1989 | Wijay et al. |
| 5,019,090 A | 5/1991 | Pinchuk |
| 5,037,427 A | 8/1991 | Harada et al. |
| 5,061,275 A | 10/1991 | Wallsten et al. |
| 5,102,417 A | 4/1992 | Palmaz |
| 5,104,404 A | 4/1992 | Wolff |
| 5,122,154 A | 6/1992 | Rhodes |
| 5,123,917 A | 6/1992 | Lee |
| 5,201,757 A | 4/1993 | Heyn et al. |
| 5,236,447 A | 8/1993 | Kubo et al. |
| 5,282,824 A | 2/1994 | Gianturco |
| 5,300,500 A | 4/1994 | Lee et al. |
| 5,314,472 A | 5/1994 | Fontaine |
| 5,330,500 A | 7/1994 | Song |
| 5,360,443 A | 11/1994 | Barone et al. |
| 5,405,377 A | 4/1995 | Cragg |
| 5,409,495 A * | 4/1995 | Osborn ............ A61M 25/10 623/1.11 |
| 5,443,495 A | 8/1995 | Buscemi et al. |
| 5,443,496 A | 8/1995 | Schwartz et al. |
| 5,443,499 A | 8/1995 | Schmitt |
| 5,449,373 A | 9/1995 | Pinchasik et al. |
| 5,507,767 A | 4/1996 | Maeda et al. |
| 5,507,771 A | 4/1996 | Gianturco |
| 5,549,663 A | 8/1996 | Cottone, Jr. |
| 5,575,816 A | 11/1996 | Rudnick et al. |
| 5,591,195 A | 1/1997 | Taheri et al. |
| 5,613,979 A | 3/1997 | Trotta et al. |
| 5,662,703 A | 9/1997 | Yurek et al. |
| 5,665,115 A | 9/1997 | Cragg |
| 5,674,241 A | 10/1997 | Bley et al. |
| 5,683,448 A | 11/1997 | Cragg |
| 5,693,086 A | 12/1997 | Goicoechea et al. |
| 5,708,044 A | 1/1998 | Branca |
| 5,725,570 A | 3/1998 | Heath |
| 5,728,150 A | 3/1998 | McDonald et al. |
| 5,735,892 A | 4/1998 | Myers et al. |
| 5,749,852 A | 5/1998 | Schwab et al. |
| 5,755,774 A | 5/1998 | Pinchuk |
| 5,756,553 A | 5/1998 | Iguchi et al. |
| 5,769,884 A | 6/1998 | Solovay |
| 5,769,887 A | 6/1998 | Brown et al. |
| 5,800,456 A | 9/1998 | Maeda et al. |
| 5,800,515 A | 9/1998 | Nadal et al. |
| 5,800,521 A | 9/1998 | Orth |
| 5,814,063 A | 9/1998 | Freitag |
| 5,824,043 A | 10/1998 | Cottone, Jr. |
| 5,824,059 A | 10/1998 | Wijay |
| 5,843,092 A | 12/1998 | Heller et al. |
| 5,843,161 A | 12/1998 | Solovay |
| 5,873,906 A | 2/1999 | Lau et al. |
| 5,876,432 A | 3/1999 | Lau et al. |
| 5,879,369 A | 3/1999 | Ishida |
| 5,891,193 A | 4/1999 | Robinson et al. |
| 5,899,934 A | 5/1999 | Amundson et al. |
| 5,906,639 A | 5/1999 | Rudnick et al. |
| 5,919,225 A | 7/1999 | Lau et al. |
| 5,922,020 A | 7/1999 | Klein et al. |
| 5,968,091 A | 10/1999 | Pinchuk et al. |
| 5,984,957 A | 11/1999 | Laptewicz et al. |
| 6,001,125 A | 12/1999 | Golds et al. |
| 6,004,348 A | 12/1999 | Banas et al. |
| 6,007,545 A | 12/1999 | Venturelli |
| 6,013,854 A | 1/2000 | Moriuchi |
| 6,015,432 A | 1/2000 | Rakos et al. |
| 6,016,846 A | 1/2000 | Knittel et al. |
| 6,022,359 A | 2/2000 | Frantzen |
| 6,022,374 A | 2/2000 | Imran |
| 6,048,360 A | 4/2000 | Khosravi et al. |
| 6,071,307 A | 6/2000 | Rhee et al. |
| 6,077,296 A | 6/2000 | Shokoohi et al. |
| 6,107,004 A | 8/2000 | Donadio, III |
| 6,123,712 A | 9/2000 | Di et al. |
| 6,139,573 A | 10/2000 | Sogard et al. |
| 6,139,575 A | 10/2000 | Shu et al. |
| 6,143,022 A | 11/2000 | Shull et al. |
| 6,146,417 A | 11/2000 | Ischinger |
| 6,159,219 A | 12/2000 | Ren |
| 6,159,239 A | 12/2000 | Greenhalgh |
| 6,165,210 A | 12/2000 | Lau et al. |
| 6,171,334 B1 | 1/2001 | Cox |
| 6,174,328 B1 | 1/2001 | Cragg |
| 6,217,609 B1 | 4/2001 | Haverkost |
| 6,231,597 B1 | 5/2001 | Deem et al. |
| 6,264,687 B1 | 7/2001 | Tomonto |
| 6,283,990 B1 | 9/2001 | Kanesaka |
| 6,283,992 B1 | 9/2001 | Hankh et al. |
| 6,287,333 B1 | 9/2001 | Appling et al. |
| 6,290,722 B1 | 9/2001 | Wang |
| 6,312,458 B1 | 11/2001 | Golds |
| 6,315,791 B1 | 11/2001 | Gingras et al. |
| 6,315,792 B1 | 11/2001 | Armstrong et al. |
| 6,331,188 B1 | 12/2001 | Lau et al. |
| 6,331,190 B1 | 12/2001 | Shokoohi et al. |
| 6,334,868 B1 | 1/2002 | Ham |
| 6,336,937 B1 | 1/2002 | Vonesh et al. |
| 6,340,366 B2 | 1/2002 | Wijay |
| 6,344,054 B1 | 2/2002 | Parodi |
| 6,350,277 B1 | 2/2002 | Kocur |
| 6,355,055 B1 | 3/2002 | Waksman et al. |
| 6,357,104 B1 | 3/2002 | Myers |
| 6,361,637 B2 | 3/2002 | Martin et al. |
| 6,364,903 B2 | 4/2002 | Tseng et al. |
| 6,387,122 B1 | 5/2002 | Cragg |
| 6,398,803 B1 | 6/2002 | Layne et al. |
| 6,409,754 B1 | 6/2002 | Smith et al. |
| 6,419,685 B2 | 7/2002 | Di et al. |
| 6,432,133 B1 | 8/2002 | Lau et al. |
| 6,436,132 B1 | 8/2002 | Patel et al. |
| 6,451,050 B1 | 9/2002 | Rudakov et al. |
| 6,461,380 B1 | 10/2002 | Cox |
| 6,464,718 B1 | 10/2002 | Miller et al. |
| 6,488,701 B1 | 12/2002 | Nolting et al. |
| 6,488,705 B2 | 12/2002 | Schmitt et al. |
| 6,497,722 B1 | 12/2002 | Von et al. |
| 6,500,203 B1 | 12/2002 | Thompson et al. |
| 6,503,556 B2 | 1/2003 | Harish et al. |
| 6,506,202 B1 | 1/2003 | Dutta et al. |
| 6,511,496 B1 | 1/2003 | Huter et al. |
| 6,520,986 B2 | 2/2003 | Martin et al. |
| 6,527,739 B1 | 3/2003 | Bigus et al. |
| 6,537,311 B1 | 3/2003 | Cox et al. |
| 6,540,773 B2 | 4/2003 | Dong |
| 6,540,776 B2 | 4/2003 | Sanders et al. |
| 6,541,589 B1 | 4/2003 | Baillie |
| 6,551,350 B1 | 4/2003 | Thornton et al. |
| 6,551,352 B2 | 4/2003 | Clerc et al. |
| 6,554,848 B2 | 4/2003 | Boylan et al. |
| 6,558,414 B2 | 5/2003 | Layne |
| 6,558,415 B2 | 5/2003 | Thompson |
| 6,565,599 B1 | 5/2003 | Hong et al. |
| 6,579,305 B1 | 6/2003 | Lashinski |
| 6,585,755 B2 | 7/2003 | Jackson et al. |

(56) References Cited

U.S. PATENT DOCUMENTS

| | | |
|---|---|---|
| 6,589,275 B1 | 7/2003 | Ivancev et al. |
| 6,589,276 B2 | 7/2003 | Pinchasik et al. |
| 6,602,284 B2 | 8/2003 | Cox et al. |
| 6,605,056 B2 | 8/2003 | Eidenschink et al. |
| 6,607,551 B1 | 8/2003 | Sullivan et al. |
| 6,616,689 B1 | 9/2003 | Ainsworth et al. |
| 6,620,128 B1 | 9/2003 | Simhambhatla |
| 6,620,193 B1 | 9/2003 | Lau et al. |
| 6,626,939 B1 | 9/2003 | Burnside et al. |
| 6,629,992 B2 | 10/2003 | Bigus et al. |
| 6,645,239 B1 | 11/2003 | Park et al. |
| 6,652,574 B1 | 11/2003 | Jayaraman |
| 6,652,579 B1 | 11/2003 | Cox et al. |
| 6,669,719 B2 | 12/2003 | Wallace et al. |
| 6,673,103 B1 | 1/2004 | Golds et al. |
| 6,689,162 B1 | 2/2004 | Thompson |
| 6,709,454 B1 | 3/2004 | Cox et al. |
| 6,712,357 B1 | 3/2004 | Tranquilla |
| 6,713,357 B1 | 3/2004 | Wang et al. |
| 6,730,117 B1 | 5/2004 | Tseng et al. |
| 6,740,114 B2 | 5/2004 | Burgermeister |
| 6,749,584 B2 | 6/2004 | Briggs et al. |
| 6,770,087 B2 | 8/2004 | Layne et al. |
| 6,770,089 B1 | 8/2004 | Hong et al. |
| 6,776,771 B2 | 8/2004 | Van et al. |
| 6,805,705 B2 | 10/2004 | Hong et al. |
| 6,849,086 B2 | 2/2005 | Cragg |
| 6,866,805 B2 | 3/2005 | Hong et al. |
| 6,872,433 B2 | 3/2005 | Seward et al. |
| 6,881,216 B2 | 4/2005 | Di et al. |
| 6,881,221 B2 | 4/2005 | Golds |
| 6,887,266 B2 | 5/2005 | Williams et al. |
| 6,893,457 B2 | 5/2005 | Dong |
| 6,923,827 B2 | 8/2005 | Campbell et al. |
| 6,945,991 B1 | 9/2005 | Brodeur et al. |
| 6,960,186 B1 | 11/2005 | Fukaya et al. |
| 7,105,018 B1 | 9/2006 | Yip et al. |
| 7,105,021 B2 | 9/2006 | Edens et al. |
| 7,108,716 B2 | 9/2006 | Burnside et al. |
| 7,112,293 B2 | 9/2006 | Dubson et al. |
| 7,115,220 B2 | 10/2006 | Dubson et al. |
| 7,118,592 B1 | 10/2006 | Dang et al. |
| 7,141,062 B1 | 11/2006 | Pinchasik et al. |
| 7,144,422 B1 | 12/2006 | Rao |
| 7,163,533 B2 | 1/2007 | Hobbs et al. |
| 7,163,553 B2 | 1/2007 | Limon |
| 7,186,263 B2 | 3/2007 | Golds et al. |
| 7,258,697 B1 | 8/2007 | Cox et al. |
| 7,273,495 B2 | 9/2007 | Limon |
| 7,288,111 B1 | 10/2007 | Holloway et al. |
| 7,314,480 B2 | 1/2008 | Eidenschink et al. |
| 7,323,008 B2 | 1/2008 | Kantor et al. |
| 7,329,276 B2 | 2/2008 | Smith et al. |
| 7,384,411 B1 | 6/2008 | Condado |
| 7,455,687 B2 | 11/2008 | Saunders et al. |
| 7,510,571 B2 | 3/2009 | Spiridigliozzi et al. |
| 7,540,879 B2 | 6/2009 | Alessandro |
| 7,578,831 B2 | 8/2009 | Von et al. |
| 7,686,841 B2 | 3/2010 | Eidenschink et al. |
| 7,691,461 B1 | 4/2010 | Prabhu |
| 7,704,274 B2 | 4/2010 | Boyle et al. |
| 7,727,271 B2 | 6/2010 | Kujawski et al. |
| 7,967,836 B2 | 6/2011 | Warnack et al. |
| 8,066,667 B2 | 11/2011 | Hayman et al. |
| 8,221,484 B2 | 7/2012 | Wesselmann |
| 8,257,432 B2 | 9/2012 | Kaplan et al. |
| 8,444,686 B2 | 5/2013 | Holman et al. |
| 8,585,640 B2 | 11/2013 | Alpini et al. |
| 8,597,566 B2 | 12/2013 | Eskaros et al. |
| 8,672,990 B2 | 3/2014 | Holman et al. |
| 8,858,863 B2 | 10/2014 | Venturelli |
| 8,926,688 B2 | 1/2015 | Burkart et al. |
| 8,979,886 B2 | 3/2015 | Campbell et al. |
| 9,149,612 B2 | 10/2015 | Chuter |
| 9,370,643 B2 | 6/2016 | Hedberg et al. |
| 9,370,647 B2 | 6/2016 | Campbell et al. |
| 9,622,888 B2 | 4/2017 | Armstrong et al. |
| 9,669,194 B2 | 6/2017 | Campbell et al. |
| 9,682,219 B2 | 6/2017 | Venturelli |
| 9,770,352 B2 | 9/2017 | Kanjickal et al. |
| 9,901,715 B2 | 2/2018 | Cully et al. |
| 9,943,428 B2 | 4/2018 | Burkart et al. |
| 10,299,948 B2 | 5/2019 | Bohn et al. |
| 10,456,281 B2 | 10/2019 | Armstrong et al. |
| 10,463,519 B2 | 11/2019 | Aggerholm et al. |
| 10,470,905 B2 | 11/2019 | Yang et al. |
| 10,543,116 B2 | 1/2020 | Bohn et al. |
| 10,568,752 B2 | 2/2020 | Kovach et al. |
| 11,779,481 B2 | 10/2023 | Kovach et al. |
| 2001/0020181 A1 | 9/2001 | Layne |
| 2001/0025130 A1 | 9/2001 | Tomonto |
| 2001/0027329 A1 | 10/2001 | Simhambhatla et al. |
| 2001/0032009 A1 | 10/2001 | Layne et al. |
| 2002/0007102 A1 | 1/2002 | Salmon et al. |
| 2002/0013617 A1 | 1/2002 | Matsutani et al. |
| 2002/0049408 A1 | 4/2002 | Van et al. |
| 2002/0077690 A1 | 6/2002 | Wang |
| 2002/0099431 A1 | 7/2002 | Armstrong et al. |
| 2002/0111668 A1 | 8/2002 | Smith |
| 2002/0151964 A1 | 10/2002 | Smith et al. |
| 2002/0165601 A1 | 11/2002 | Clerc |
| 2003/0060756 A1 | 3/2003 | Hayman et al. |
| 2003/0114909 A1 | 6/2003 | Clerc et al. |
| 2003/0208260 A1 | 11/2003 | Lau et al. |
| 2003/0236563 A1 | 12/2003 | Fifer |
| 2004/0019373 A1 | 1/2004 | Casey et al. |
| 2004/0024442 A1 | 2/2004 | Sowinski et al. |
| 2004/0024448 A1 | 2/2004 | Chang et al. |
| 2004/0030377 A1 | 2/2004 | Dubson et al. |
| 2004/0033364 A1 | 2/2004 | Spiridigliozzi et al. |
| 2004/0096532 A1 | 5/2004 | Dubson et al. |
| 2004/0096533 A1 | 5/2004 | Dubson et al. |
| 2004/0106980 A1 | 6/2004 | Solovay et al. |
| 2004/0138731 A1* | 7/2004 | Johnson ............... A61F 2/958 623/1.11 |
| 2004/0143272 A1 | 7/2004 | Cully et al. |
| 2004/0167635 A1 | 8/2004 | Yachia et al. |
| 2004/0172127 A1 | 9/2004 | Kantor |
| 2004/0236402 A1 | 11/2004 | Layne et al. |
| 2005/0004647 A1 | 1/2005 | Bassoe |
| 2005/0010281 A1 | 1/2005 | Yodfat et al. |
| 2005/0125071 A1 | 6/2005 | Nahleili |
| 2005/0137675 A1 | 6/2005 | Dubson et al. |
| 2005/0154449 A1 | 7/2005 | Elmaleh |
| 2005/0182474 A1 | 8/2005 | Jones et al. |
| 2005/0186243 A1 | 8/2005 | Hunter et al. |
| 2005/0209672 A1 | 9/2005 | George et al. |
| 2005/0228480 A1 | 10/2005 | Douglas et al. |
| 2006/0009835 A1 | 1/2006 | Osborne et al. |
| 2006/0036308 A1 | 2/2006 | Goshgarian |
| 2006/0036311 A1 | 2/2006 | Nakayama et al. |
| 2006/0085065 A1 | 4/2006 | Krause et al. |
| 2006/0122691 A1 | 6/2006 | Richter |
| 2006/0184237 A1 | 8/2006 | Weber et al. |
| 2006/0190072 A1 | 8/2006 | Das |
| 2006/0259133 A1 | 11/2006 | Sowinski et al. |
| 2006/0266474 A1 | 11/2006 | Burnside et al. |
| 2006/0271091 A1 | 11/2006 | Campbell et al. |
| 2006/0271157 A1 | 11/2006 | Edens et al. |
| 2006/0271165 A1 | 11/2006 | Yip et al. |
| 2006/0287709 A1 | 12/2006 | Rao |
| 2006/0293743 A1 | 12/2006 | Andersen et al. |
| 2007/0055365 A1 | 3/2007 | Greenberg et al. |
| 2007/0073383 A1 | 3/2007 | Yip et al. |
| 2007/0129791 A1 | 6/2007 | Balaji |
| 2007/0208412 A1 | 9/2007 | Elmaleh |
| 2007/0213804 A1 | 9/2007 | Kaplan et al. |
| 2007/0239264 A1 | 10/2007 | Fliedner |
| 2007/0250146 A1 | 10/2007 | Cully et al. |
| 2008/0161901 A1 | 7/2008 | Heuser et al. |
| 2008/0319388 A1 | 12/2008 | Slattery et al. |
| 2009/0018635 A1 | 1/2009 | Holman et al. |
| 2009/0054967 A1 | 2/2009 | Das |
| 2009/0069878 A1 | 3/2009 | Weber et al. |

(56) References Cited

U.S. PATENT DOCUMENTS

| | | |
|---|---|---|
| 2009/0112306 A1 | 4/2009 | Bonsignore et al. |
| 2009/0138070 A1 | 5/2009 | Holzer et al. |
| 2009/0182413 A1 | 7/2009 | Burkart et al. |
| 2009/0234429 A1 | 9/2009 | Lau |
| 2009/0283206 A1 | 11/2009 | Eskaros et al. |
| 2010/0069839 A1 | 3/2010 | Holman et al. |
| 2010/0222870 A1 | 9/2010 | Kaplan et al. |
| 2010/0228333 A1 | 9/2010 | Drasler et al. |
| 2011/0046717 A1 | 2/2011 | Issenmann et al. |
| 2011/0087191 A1 | 4/2011 | Scheuermann |
| 2011/0264192 A1 | 10/2011 | Hartley et al. |
| 2012/0071912 A1* | 3/2012 | Campbell ............. A61M 25/10 606/192 |
| 2012/0109283 A1 | 5/2012 | Burkart et al. |
| 2012/0253380 A1 | 10/2012 | Venturelli |
| 2012/0330232 A1 | 12/2012 | Hedberg et al. |
| 2013/0018406 A1 | 1/2013 | Campbell et al. |
| 2013/0184807 A1 | 7/2013 | Kovach et al. |
| 2013/0253466 A1* | 9/2013 | Campbell ......... A61M 25/1029 604/103.05 |
| 2013/0261731 A1 | 10/2013 | Zhou et al. |
| 2014/0066896 A1 | 3/2014 | Tilson et al. |
| 2014/0066897 A1 | 3/2014 | Campbell et al. |
| 2014/0066898 A1 | 3/2014 | Cully et al. |
| 2014/0135891 A1 | 5/2014 | Poehlmann et al. |
| 2014/0142684 A1 | 5/2014 | Zukowski |
| 2014/0172066 A1 | 6/2014 | Goepfrich et al. |
| 2014/0276406 A1 | 9/2014 | Campbell et al. |
| 2014/0277331 A1 | 9/2014 | Ngo et al. |
| 2014/0277346 A1 | 9/2014 | Kanjickal et al. |
| 2014/0277374 A1 | 9/2014 | Kovach |
| 2014/0378896 A1 | 12/2014 | Venturelli |
| 2015/0133988 A1 | 5/2015 | Chuter |
| 2016/0143759 A1 | 5/2016 | Bohn et al. |
| 2016/0243340 A1 | 8/2016 | Campbell et al. |
| 2017/0172776 A1 | 6/2017 | Kanjickal et al. |
| 2017/0340464 A1 | 11/2017 | Kovach et al. |
| 2017/0340465 A1 | 11/2017 | Kanjickal et al. |
| 2017/0348124 A1 | 12/2017 | Wang |
| 2018/0049898 A1 | 2/2018 | Armstrong et al. |
| 2018/0193177 A1 | 7/2018 | Burkart et al. |
| 2018/0296377 A1 | 10/2018 | Bohn et al. |
| 2019/0209739 A1 | 7/2019 | Goepfrich et al. |
| 2019/0298556 A1 | 10/2019 | Bohn et al. |
| 2019/0388252 A1 | 12/2019 | Armstrong et al. |
| 2020/0253763 A1 | 8/2020 | Kovach et al. |
| 2021/0236314 A1 | 8/2021 | Bohn et al. |
| 2021/0361451 A1 | 11/2021 | Burkart et al. |
| 2022/0168124 A1 | 6/2022 | Bohn et al. |
| 2024/0082031 A1 | 3/2024 | Bohn et al. |
| 2024/0173154 A1 | 5/2024 | Burkart et al. |

FOREIGN PATENT DOCUMENTS

| | | |
|---|---|---|
| CN | 101909545 A | 12/2010 |
| CN | 102940543 A | 2/2013 |
| CN | 103260549 A | 8/2013 |
| CN | 103561686 A | 2/2014 |
| CN | 103702709 A | 4/2014 |
| CN | 103930157 A | 7/2014 |
| CN | 103930158 A | 7/2014 |
| CN | 105050550 A | 11/2015 |
| EP | 0745395 A2 | 12/1996 |
| EP | 0951877 A2 | 10/1999 |
| EP | 1110561 A2 | 6/2001 |
| EP | 1550477 A1 | 7/2005 |
| EP | 1927327 A2 | 6/2008 |
| JP | 09-099087 A | 4/1997 |
| JP | 11-299901 A | 11/1999 |
| JP | 2002-501404 A | 1/2002 |
| JP | 2005-535414 A | 11/2005 |
| JP | 2010-500107 A | 1/2010 |
| JP | 2011-206124 A | 10/2011 |
| JP | 2014-520632 A | 8/2014 |
| JP | 2014-530045 A | 11/2014 |
| JP | 2015-534883 A | 12/2015 |
| JP | 2016-506271 A | 3/2016 |
| WO | 95/17223 A1 | 6/1995 |
| WO | 95/26695 A2 | 10/1995 |
| WO | 96/21404 A1 | 7/1996 |
| WO | 96/38109 A1 | 12/1996 |
| WO | 98/31305 A1 | 7/1998 |
| WO | 99/17680 A1 | 4/1999 |
| WO | 99/34855 A1 | 7/1999 |
| WO | 00/42949 A2 | 7/2000 |
| WO | 00/43051 A1 | 7/2000 |
| WO | 00/45741 A1 | 8/2000 |
| WO | 00/49971 A1 | 8/2000 |
| WO | 01/21101 A1 | 3/2001 |
| WO | 02/22024 A2 | 3/2002 |
| WO | 03/13337 A2 | 2/2003 |
| WO | 03/07795 A3 | 4/2003 |
| WO | 03/57075 A2 | 7/2003 |
| WO | 03/57077 A1 | 7/2003 |
| WO | 2004/016199 A1 | 2/2004 |
| WO | 2004/093941 A2 | 11/2004 |
| WO | 2005/096997 A2 | 10/2005 |
| WO | 2006/029617 A1 | 3/2006 |
| WO | 2006/081568 A1 | 8/2006 |
| WO | 2006/124824 A1 | 11/2006 |
| WO | 2008/019022 A1 | 2/2008 |
| WO | 2009/009635 A1 | 1/2009 |
| WO | 2009/066330 A1 | 5/2009 |
| WO | 2010/037141 A1 | 4/2010 |
| WO | 2013/009740 A1 | 1/2013 |
| WO | 2013/040522 A2 | 3/2013 |
| WO | 2013/096854 A3 | 8/2013 |
| WO | 2013/162685 A1 | 10/2013 |
| WO | 2014/078558 A1 | 5/2014 |
| WO | 2014/152684 A2 | 9/2014 |
| WO | 2014/158516 A1 | 10/2014 |
| WO | 2015/073114 A1 | 5/2015 |
| WO | 2016/086202 A2 | 6/2016 |
| WO | 2017/204838 A1 | 11/2017 |
| WO | 2018/039444 A1 | 3/2018 |

OTHER PUBLICATIONS

International Search Report and Written Opinion issued in PCT/US2016/039565, mailed Oct. 10, 2016, 20 pages.

Nakayama Y, Nishi S, Ueda H, et al. Fabrication of micropored elastomeric film covered stents and acute-phase performances. Development of Covered Stents 2002; 52-61.

Nishi S, Nakayama Y, Ueda H, et al. Newly developed stent graft with micropored and heparin impregnated SPU film Long-term follow-up study in vivo. 2001 (Suppl 1) 161-166.

Wilson EP, White RA, Kopchok GE, et al. Deployment and Healing of an ePTFE Encapsulated Stent Endograft in the Canine Aorta. Annals of Vascular Surgery 1997; v11, n4:354-358.

\* cited by examiner

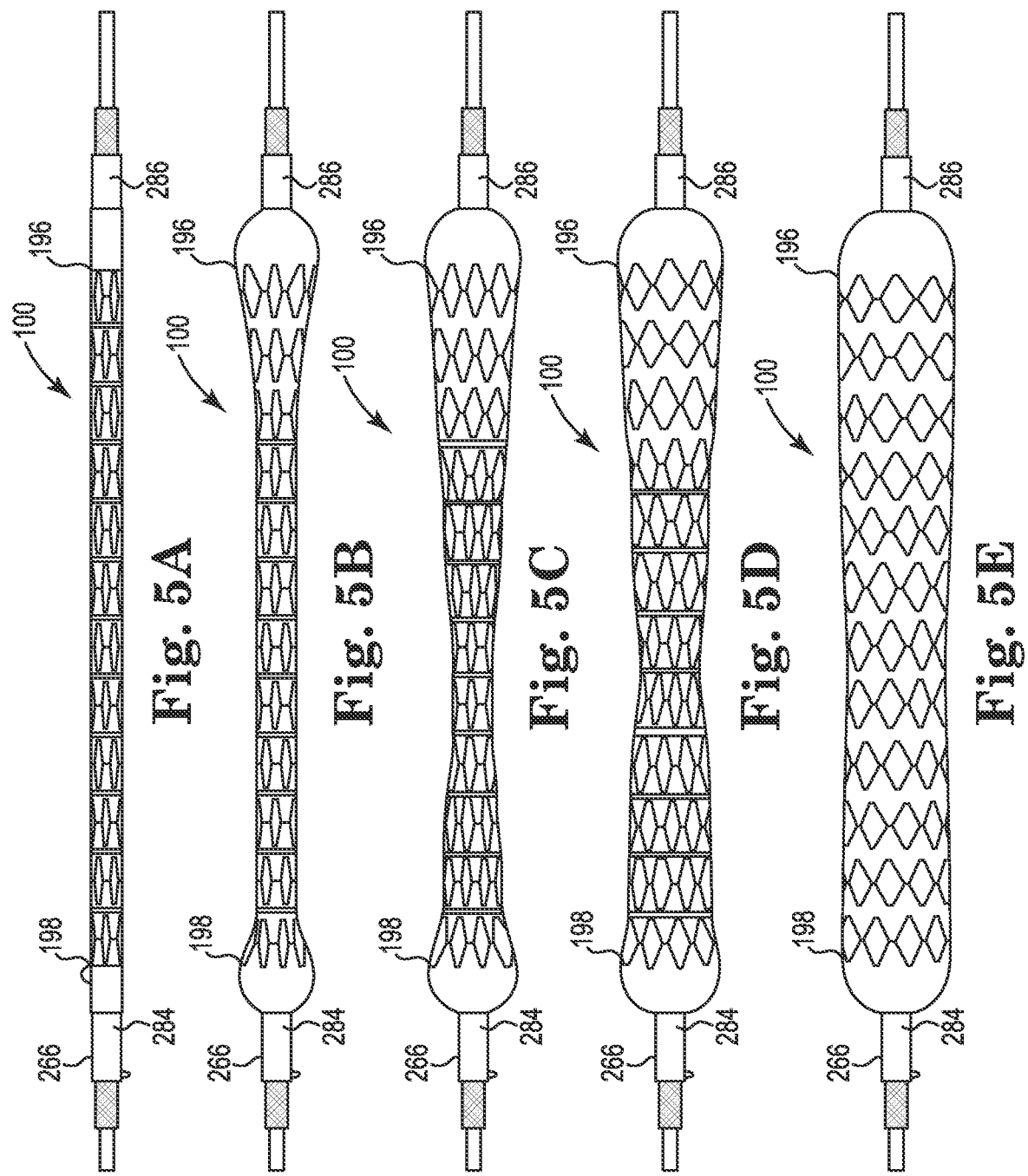

CONTROLLED ENDOPROSTHESIS BALLOON EXPANSION

CROSS-REFERENCE TO RELATED APPLICATION

This application is a continuation of U.S. patent application Ser. No. 16/783,520, filed Feb. 6, 2020, which is a continuation of U.S. patent application Ser. No. 15/164,657, filed May 25, 2016, now U.S. Pat. No. 10,568,752, issued Feb. 25, 2020, which are incorporated herein by reference in their entireties for all purposes.

FIELD

The present disclosure generally relates to endoprosthesis delivery systems, and more particularly, to balloon expansion delivery systems.

BACKGROUND

Endoprostheses are valuable tools for improving and saving lives. In many instances, an endoprosthesis is inserted into a vasculature in an "undeployed" state and must be expanded into a "deployed" state. To transition the endoprosthesis between these two states, a balloon may be located within the endoprosthesis in its undeployed state and inflated, with the expansion of the balloon pushing the endoprosthesis into its deployed state.

SUMMARY OF THE DISCLOSURE

This disclosure is generally directed to medical assemblies including balloon expandable endoprostheses. In various examples, an endoprosthesis delivery system can include a layer within, over, or along a balloon configured to counteract variable resistance of an endoprosthesis to expansion of the balloon during deployment. Some examples include a cover over the balloon configured to pause or slow expansion of balloon at a partially deployed or intermediate diameter of the balloon or stent until a pressure within the balloon overcomes resistance to expansion of the cover (e.g., a yield strength of the cover). Such examples may mitigate uneven expansion of a stent about a length of the stent during deployment of the stent.

In one variation, a medical assembly includes a balloon expandable endoprosthesis having a first end and a second end and comprising a plurality of ringed stent elements flexibly connected to each other via at least one flexible connector, with ringed stent elements proximate the first end and the second end, the endoprosthesis being deployable from an undeployed state with an undeployed diameter to a deployed state with a deployed diameter. The medical assembly further includes a catheter assembly onto which the endoprosthesis is assembled, the catheter assembly comprising a balloon, and a cover along the balloon. The endoprosthesis is coaxially located about the balloon and the cover. One or more portions of the balloon and the cover reach an intermediate diameter between the undeployed diameter and the deployed diameter in which the portions of the balloon and the cover are inflated by increasing an inflation pressure within the balloon and approximately maintained at about the intermediate diameter until the inflation pressure increases by at least 1 atmosphere to overcome a yield strength of the cover.

In some examples, the one or more portions of the balloon and the cover that reach the intermediate diameter until the inflation pressure increases by at least 1 atmosphere to overcome a yield strength of the cover include end portions of the balloon and the cover, and a middle portion of the balloon and the cover remain smaller than intermediate diameter until after the inflation pressure increases by the at least 1 atmosphere.

In some examples, the one or more portions of the balloon and the cover that reach the intermediate diameter until the inflation pressure increases by at least 1 atmosphere to overcome a yield strength of the cover includes substantially all portions of the balloon and the cover adjacent to the endoprosthesis such that each of the plurality of ringed stent elements approximately reach the intermediate diameter until the inflation pressure increases by the at least 1 atmosphere to overcome a yield strength of the cover.

In some examples, the endoprosthesis includes a stent-graft, the flexible connector includes a graft material, and plurality of ringed stent elements are connected to one another only via nonmetallic materials including the flexible connector.

In some examples, the flexible connector includes flexible longitudinal connectors.

In some examples, a profile of the medical assembly as measured about the endoprosthesis in the undeployed state is between about 5 to about 10 French.

In some examples, a thickness of the cover on the medical assembly in the undeployed state is between about 0.025 to about 0.051 millimeters.

In some examples, a radial strength of the cover provides resistance to inflation of the balloon and is configured to counteract variable resistance of the endoprosthesis to expansion of the balloon to mitigate uneven expansion of the endoprosthesis during expansion from the undeployed diameter to the deployed diameter.

In some examples, the cover concentrically surrounds the balloon about an entire length of the balloon.

In some examples, the cover provides a greater radial strength at one or both ends of the balloon as compared to a radial strength at a middle portion of the balloon.

In some examples, the cover comprises a frangible layer designed to rupture at the intermediate diameter with the ultimate strength of the frangible layer contributing to the yield strength of the cover to resist expansion beyond the intermediate diameter.

In some examples, the cover comprises a pre-stretched layer configured to provide increased resistance to expansion due to the yield strength of the cover to resist expansion beyond the intermediate diameter.

In some examples, the balloon includes a material selected from a group consisting of: a compliant material, a semi-compliant material, and a noncompliant material.

In some examples, the deployed diameter is at least 11 millimeters.

In some examples, the cover is configured to limit uneven expansion of adjacent ringed stent elements during deployment to prevent a foreshortening force due to uneven expansion of adjacent ringed stent elements from exceeding a frictional force between the cover and the endoprosthesis, and due to the limited uneven expansion of adjacent ringed stent elements, the endoprosthesis does not foreshorten during expansion from the undeployed diameter to the deployed diameter.

In another variation, a method of implanting an endoprosthesis comprises inserting a distal end of a medical assembly into a vasculature of a patient. The medical assembly comprises a balloon expandable endoprosthesis having a first end and a second end and comprising a plurality of ringed stent elements flexibly connected to each other via at least one flexible connector, with ringed stent elements proximate the first end and the second end, the endoprosthesis being deployable from an undeployed state with an undeployed diameter to a deployed state with a deployed diameter, and a catheter assembly onto which the endoprosthesis is assembled, the catheter assembly comprising a balloon, and a cover along the balloon. The endoprosthesis is coaxially located about the balloon and the cover. One or more portions of the balloon and the cover reach an intermediate diameter between the undeployed diameter and the deployed diameter in which the portions of the balloon and the cover are inflated by increasing an inflation pressure within the balloon and approximately maintained at about the intermediate diameter until the inflation pressure increases by at least 1 atmosphere to overcome a yield strength of the cover. The method further comprises, delivering, with the medical assembly, the endoprosthesis mounted over the balloon to a treatment site within the vasculature of the patient or another vasculature of the patient, and remotely inflating the balloon to expand the endoprosthesis from the undeployed diameter to the deployed diameter.

In another variation, a method of making a deployment system comprises assembling a balloon expandable endoprosthesis having a first end and a second end to a catheter assembly comprising an expandable balloon and a cover such that the endoprosthesis is mounted over the balloon and the cover with the endoprosthesis being deployable via expansion of the balloon, the endoprosthesis providing an undeployed diameter, and a deployed diameter. The endoprosthesis comprises a plurality of ringed stent elements flexibly connected to each other via at least one flexible connector, with ringed stent elements proximate the first end and the second end, the endoprosthesis being deployable from an undeployed state with an undeployed diameter to a deployed state with a deployed diameter. One or more portions of the balloon and the cover reach an intermediate diameter between the undeployed diameter and the deployed diameter in which the portions of the balloon and the cover are inflated by increasing an inflation pressure within the balloon and approximately maintained at about the intermediate diameter until the inflation pressure increases by at least 1 atmosphere to overcome a yield strength of the cover.

In some examples, the method further comprises, prior to assembling the endoprosthesis to the catheter assembly, pre-stretching the cover by inflating the balloon and the cover to the intermediate diameter.

In another variation, a medical assembly comprises a balloon expandable endoprosthesis having a first end and a second end and comprising a plurality of ringed stent elements flexibly connected to each other via at least one flexible connector, with ringed stent elements proximate the first end and the second end, the endoprosthesis being deployable from an undeployed state with an undeployed diameter to a deployed state with a deployed diameter, and a catheter assembly onto which the endoprosthesis is assembled, the catheter assembly comprising a balloon, and a cover coupled to the balloon, wherein the endoprosthesis is coaxially located about the balloon and the cover. The deployed diameter is at least 11 millimeters. The cover is configured to limit uneven expansion of adjacent ringed stent elements during deployment to prevent a foreshortening force due to uneven expansion of adjacent ringed stent elements from exceeding a frictional force between the cover and the endoprosthesis. Due to the limited uneven expansion of adjacent ringed stent elements, the endoprosthesis does not foreshorten during expansion from the undeployed diameter to the deployed diameter.

In some examples, the limited uneven expansion of adjacent ringed stent elements results in an angle of no greater than 35 degrees relative to a longitudinal axis of the endoprosthesis.

In some examples, one or more portions of the balloon and the cover reach an intermediate diameter between the undeployed diameter and the deployed diameter in which the portions of the balloon and the cover are inflated by increasing an inflation pressure within the balloon and approximately maintained at about the intermediate diameter until the inflation pressure increases by at least 1 atmosphere to overcome a yield strength of the cover.

BRIEF DESCRIPTION OF THE DRAWINGS

The features and advantages of the present disclosure will become more apparent from the detailed description set forth below when taken in conjunction with the drawings.

FIGS. 5A-5E illustrate side views of an endoprosthesis delivery system in accordance with in various stages of deployment.

DETAILED DESCRIPTION

Figure 1A:
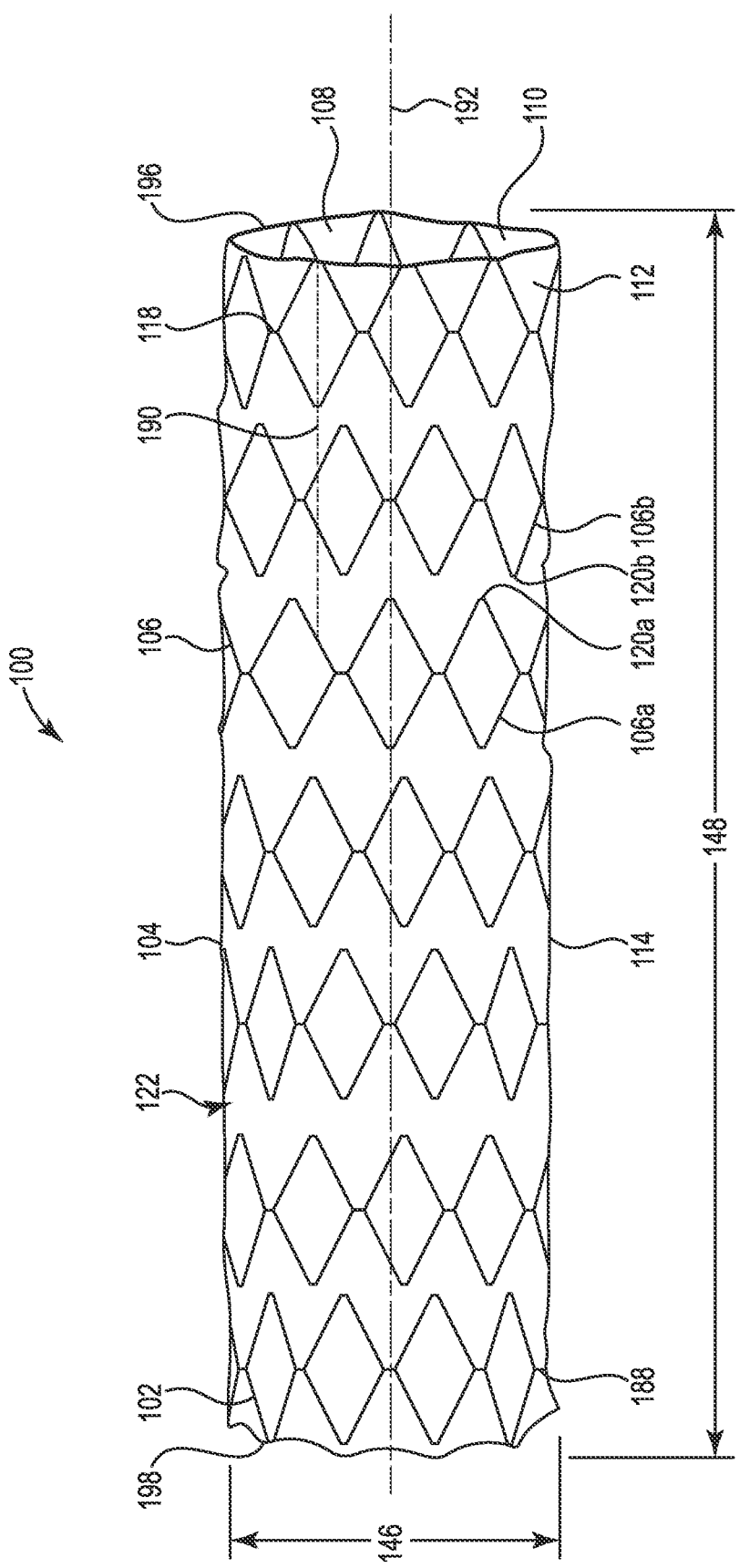
FIGS. 1A and 1B illustrate side views of a balloon expandable stent-graft.

An endoprosthesis can be inserted into a vasculature in an "undeployed" state and expanded into a "deployed" state. To transition the endoprosthesis between these two states, a balloon may be located within the endoprosthesis in its undeployed state and inflated, with the expansion of the balloon pushing the endoprosthesis into its deployed state. However, the balloon can extend beyond the longitudinal length of the endoprosthesis. As a result, those portions of the balloon unconstrained by the endoprosthesis expand rapidly in comparison to those portions of the balloon within the endoprosthesis, causing the balloon to exert a longitudinal force on the endoprosthesis that causes the endoprosthesis to diminish in longitudinal length. Aspects of the present disclosure can reduce that effect, among other potential features and benefits discussed below in more detail.

The terms "endoprosthetic device," "endoprosthesis," "vascular device," and the like can refer, throughout the specification and in the claims, to any medical device capable of being implanted and/or deployed within a body lumen. An endoprosthesis may include a stent, a stent-graft, a graft, a filter, an occluder, a balloon, a lead, and energy transmission device, a deployable patch, an indwelling catheter, and the like.

In addition, throughout this specification and claims, the delivery systems described herein can, in general, include an endoprosthesis constrained by a "cover" or "sheath." The cover or sheath may include a sheet of material that is fitted about an endoprosthesis. As used throughout the specification and in the claims, the term "elongate member" can refer to a shaft-like structure such as a catheter, guidewire, introducer sheath, or the like. An endoprosthesis may be mounted or loaded on a catheter, also referred to herein as an inner shaft, and, in a constrained diameter, fit within an introducer sheath, also referred to herein as an outer shaft.

Further, the term "distal" refers to a relative location that is farther from a location in the body at which the medical device was introduced. Similarly, the term "distally" refers to a direction away from a location in the body at which the medical device was introduced.

The term "proximal" refers to a relative location that is closer to the location in the body at which the medical device was introduced. Similarly, the term "proximally" refers to a direction towards a location in the body at which the medical device was introduced.

With continuing regard to the terms proximal and distal, this disclosure should not be narrowly construed with respect to these terms. Rather, the devices and methods described herein may be altered and/or adjusted relative to the anatomy of a patient.

As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

As used herein, the term "vessel" refers to any luminal or tubular structure within the body to which these constructs may be utilized. This includes, but is not limited to, vascular blood vessels, vascular defects such as arteriovenous malformations, aneurysm, or others, vessels of the lymphatic system, esophagus, intestinal anatomy, sinuous cavity, urogenital system, or other such systems or anatomical features. Techniques disclosed herein may also be suitable for the treatment of a malignant disease (e.g., cancer) within or associated with a vessel.

Figure 1B:
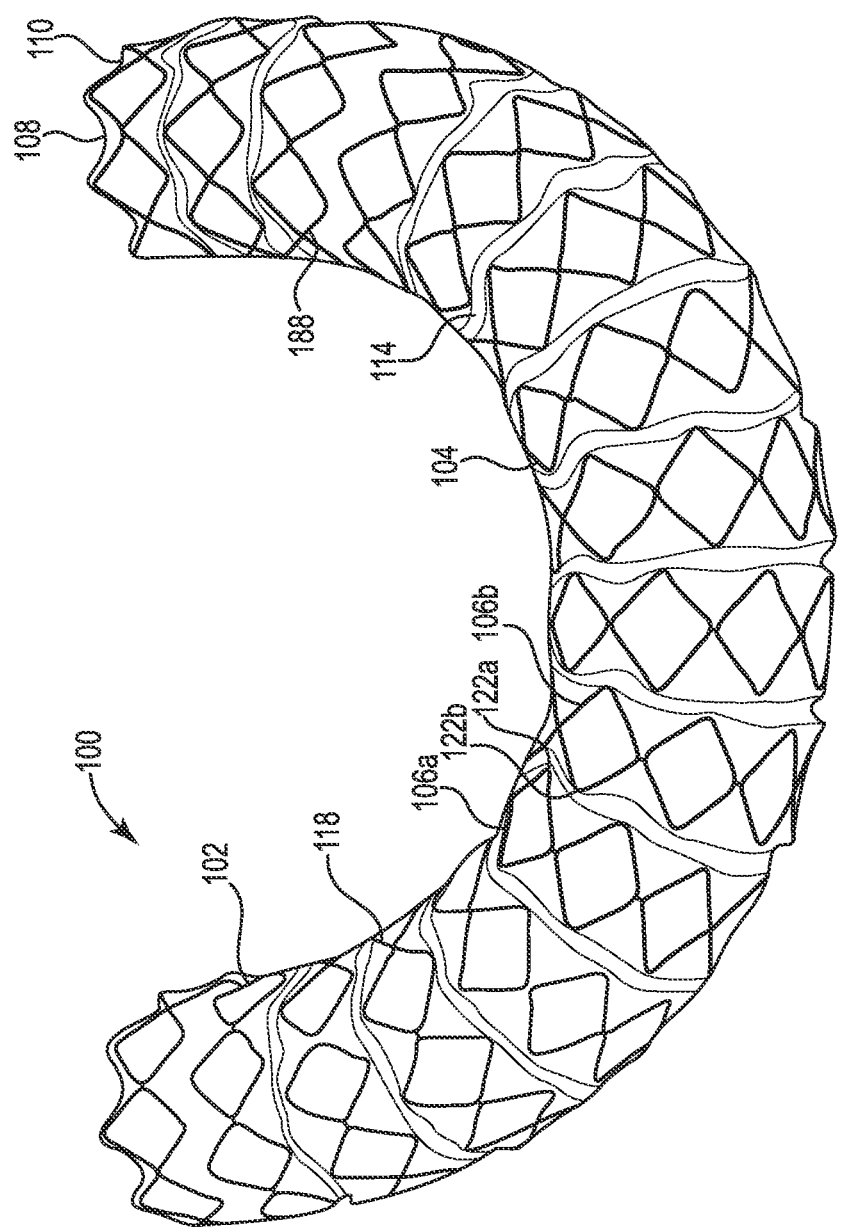

FIGS. 1A and 1B illustrate a balloon expandable stent-graft 100. Stent-graft 100 is one example of an endoprosthesis and includes graft member 114 and stent member 102 with ringed stent elements 104.

As described in further detail below, stents, such as stent-graft 100, can be deployed on a balloon. The end elements of ringed stent elements 104 are not constrained by adjacent elements and deploy at a lower expansion force than the rest of ringed stent elements 104. With a simple deployment balloon having a consistent profile, during deployment, the end elements of ringed stent elements 104 will grow larger than the other elements of ringed stent elements 104. This creates an axially compressive force as the ringed stent elements 104 are pushed from the highest expansion portion of the balloon on the ends to the less expanded portion of the balloon towards the middle. The axial foreshortening force is a function of the angle of the balloon due to uneven expansion at the end element of ringed stent elements 104. As the angle increases, the axially compressive forces can increase, and as axially compressive forces increase, likelihood of foreshortening increases. The axial force from the balloon is resisted by the combination of the friction between the stent, or stent graft, and the balloon and the stiffness of the weakest longitudinal portions of the endoprosthesis. When the axial force from the balloon exceeds the frictional forces, axial foreshortening can occur.

The angle is a function of the difference in diameter across the width of an end element of ringed stent elements 104. A larger diameter difference results in a larger angle and can therefore result in a greater foreshortening force. Larger diameter stents are capable of larger diameter differences during deployment. Foreshortening forces can be a function of the size of the deployed stents, with higher foreshortening forces during deployment of larger stents. For larger stents, such as stents of equal to or greater than 11 millimeters, from about 12 to about 16 millimeters, or even 16 millimeters or greater, the angle may be enough to overcome frictional forces between the end elements of ringed stent elements 104 and the balloon, leading to axial foreshortening. Although, undesirable foreshortening during deployment can also occur with stents of less than 11 millimeters.

In addition to undesirable foreshortening, slipping of the end elements of ringed stent elements 104 can interfere with the expansion of neighboring elements. For example, an end element of ringed stent elements 104 may slip during deployment until overlapping the adjacent element. The overlapping of the end element of ringed stent elements 104 with the adjacent element may interfere with the full expansion of the adjacent element. Furthermore, because the spacing between the end element of and the adjacent element ringed stent elements 104 is shortened, the low-force bend radius of stent-graft 100 may be compromised in that the adjacent ringed stent elements 104 may contact one another on an inside of the curve with little or no bending.

As disclosed herein, reducing the angle of the balloon due to uneven expansion mitigates axial foreshortening of stent-graft 100 during deployment. In some examples, a cover on a balloon may create an intermediate partial deployment diameter for all or a portion of length of stent-graft 100, such as the ends, to reduce the maximum balloon angle during deployment to be no more than 35 degrees, such as no more than 20 degrees or even no more than 10 degrees. In some examples, a balloon and a cover or portions thereof are inflated by increasing an inflation pressure within the balloon until reaching an intermediate diameter between an undeployed diameter and a deployed diameter, and approximately maintained at about the intermediate diameter until the inflation pressure increases to overcome a yield strength of the cover.

Endoprosthesis with high bending flexibility are more susceptible to foreshortening. The bending flexibility of an endoprosthesis is determined in part by connectors between ringed stent elements. Connectors between ringed stent elements can be rigid or can compress, fold or bend. Generally, bending flexibility of an endoprosthesis requires that connectors on the inside of the curve shorten, and/or connectors on the outside of the curve lengthen. The stiffness of these connectors in an endoprosthesis affects the bending flexibility as well as foreshortening flexibility and elongation flexibility.

As used herein, the term "longitudinal stent elements" includes stent elements representing the portions of the stent interconnecting ringed stent elements, though the stent elements need not extend parallel to the longitudinal axis (e.g., angled, undulating, or other paths that include a longitudinal component are contemplated). Generally, longitudinal stent elements provide less longitudinal stiffness than ringed stent elements. Accordingly, the stiffness of longitudinal stent elements may be the primary factor in resistance to bending, foreshortening and elongation of the stent.

In some examples, the connectors include longitudinal elements such as longitudinal stent elements (generally metal), or longitudinal elements formed from a compliant material, such as a graft material. Metal longitudinal stent elements may be generally stiffer than longitudinal elements formed from more compliant materials, although the design of longitudinal stent elements, such as their profile and thickness, affects the stiffness of longitudinal stent elements such that longitudinal stent elements may be selected to provide a wide range of bending flexibilities in the design of an endoprosthesis.

Stent-graft 100 has a bending flexibility determined only by the stiffness of graft member 114 up until adjacent ringed stent elements 104 contact one another on an inside of the curve, which is generally minimal. For example, stent-graft 100 may require a bending force of 5 Newtons or less up until adjacent ringed stent elements 104 contact one another on an inside of the curve. Furthermore, the spacing between adjacent ringed stent elements 104 relative to the longitudinal widths of adjacent ringed stent elements 104 affects the low-force bend radius of stent-graft 100 as the low-force bend radius of stent-graft 100 is the radius of the curve of stent-graft 100 when adjacent ringed stent elements 104 contact one another on an inside of the curve.

In addition to affecting bending flexibility, longitudinal stent elements, or the lack thereof, further affect column strength and forces required for axial foreshortening. Longitudinal stent elements generally help resist axial forces applied during deployment to reduce foreshortening. In contrast, stent-graft 100, which does not include longitudinal stent elements between independent ringed stent elements 104, is connected only by graft member 114. Thus, foreshortening of stent-graft 100 may occur in response to relatively low compressive forces in the axial direction. Such axially compressive forces may occur from uneven balloon expansion during deployment. For example, if the ends of the balloon expand first, then the further expansion of the balloon will tend to compress ringed stent elements closer to each other. This effect can be exacerbated at larger diameters.

Design of a stent often includes tradeoffs between providing a high radial force once deployed with high bending flexibility and low axial foreshortening. For example, a stent with relatively stiff longitudinal stent elements will generally provide low axial foreshortening but more bending stiffness. In contrast, stent-graft 100, which does not include longitudinal stent elements between independent ringed stent elements 104, generally provides a low bending stiffness, but is more readily subject to foreshortening during deployment. Although an endoprosthesis with more flexible longitudinal stent elements is also more readily subject to foreshortening during deployment than an endoprosthesis with higher stiffness longitudinal stent elements.

In the particular example of stent-graft 100, stent-graft 100 includes independent ring stent elements 104 without longitudinal elements connecting adjacent stent elements. Instead, graft member 114 represents a flexible connector connecting adjacent independent ring stent elements 104. In this manner, ring stent elements 104 are connected to one another only via nonmetallic materials such as graft member 114. Graft member 114 tends to limit only the fully extended length stent-graft 100 with limited resistance to foreshortening or bending.

While stent-graft 100 is described as not including longitudinal elements, alternatively, stent-graft 100 may include flexible connectors such as longitudinal elements formed from a PTFE material, a nylon material or other flexible material or longitudinal stent elements of low bending stiffness. Such flexible longitudinal elements may aid in the manufacture of stent-graft 100 by holding ringed stent elements 104 in predetermined positions relative to each other during the attachment of graft member 114 with ringed stent elements 104. Graft 14 also represents a flexible connector flexibly connecting adjacent ringed stent elements 104. The mechanical properties of stent-graft 100 with flexible connectors flexibly connecting adjacent ringed stent elements 104 are similar whether the flexible connectors include discrete longitudinal stent elements of low bending stiffness, longitudinal elements formed from a flexible material and/or graft 14.

With reference to stent-graft 100 in FIG. 1A, ringed stent elements 104 can include, for example, interconnected wire frames 106 arranged in a circular pattern. For example, ringed stent elements 104 can include a single row of interconnected wire frames 106. One or more points 118 of a wire frame 106 may be in contact with and connected to points 118 of adjacent wire frames 106. In some examples, ringed stent elements 104 can include a multiplicity of individual wire frames 106 formed independently of one another and connected to each other at one or more points 118, either directly or by longitudinal stent elements (not included in stent-graft 100) between ringed stent elements 104. In other examples, wire frames 106 are formed together as a single interconnected stent element 104.

Wire frames 106 can include a polygon, such as, for example, a parallelogram. In some examples, wire frames 106 include a diamond shape. In other examples, wire frames 106 can include a square or rectangular shape. Any shape of wire frames 106, including shapes that are not polygonal (such as ovoid or rounded shapes) or shapes that include undulations or bends, are within the scope of the present disclosure.

In some examples, wire frames 106 include a metal material. For example, wire frames 106 can include steel, such as stainless steels or other alloys. In other examples, wire frames 106 can include a shape memory alloy, such as, for example, Nitinol. In yet other examples, wire frames 106 include a non-metallic material, such as a polymeric material. Further, the material of wire frames 106 may be permanent (i.e., non-bioabsorbable) or bioabsorbable. Any material of wire frames 106 having sufficient strength is within the scope of the present disclosure.

For example, ringed stent elements 104 can be cut from a single metallic tube. In some examples, ringed stent elements 104 are laser cut from a stainless steel tube. However, any manner of forming ringed stent elements 104 and/or wire frames 106 is within the scope of the present disclosure.

As previously mentioned, stent-graft 100 further includes a graft member 114. Graft member 114 may, for example, provide a lumen through which blood may flow from one end to another and can include a number of layers or elements secured together to form a single graft member 114.

Graft member 114 can include, for example, an inner graft element 108. In some examples, stent member 102 is positioned concentrically around inner graft element 108. For example, inner graft element 108 can include a layer of polymeric material having a luminal surface 110 that is in contact with blood flow within a vessel. Stent member 102 can surround, be in contact with, and provide support to inner graft element 108.

Graft member 114 can further include, for example, an outer graft element 112. In some examples, outer graft element 112 concentrically surrounds at least a portion of stent member 102. For example, outer graft element 112 can concentrically surround stent member 102 and inner graft element 108, essentially sandwiching ringed stent elements 104 of stent member 102 between the two graft elements 108 and 112.

Inner graft element 108 and outer graft element 112 can include one or more of, for example, expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Outer graft element 112 can include high strength polymer fibers such as ultra-high molecular weight polyethylene fibers (e.g., Spectra®, Dyneema Purity®, etc.) or aramid fibers (e.g., Technora®, etc.). Further, outer graft element 112 can include one or more layers of polymeric material, and may be a tube or a wrapped element as described in connection with inner graft element 108. In some examples, inner graft element 108 and outer graft element 112 include the same polymeric material. In other examples, inner graft element 108 and outer graft element 112 include different polymeric materials.

In such examples, inner graft element 108 and outer graft element 112 can orient and maintain the position of each of a multiplicity of ringed stent element 104 such that graft 14 serves a flexible connector of stent-graft 100. For example, each ringed stent element 104 of stent member 102 may be positioned at a desired location along inner graft element 108 and then surrounded by outer graft element 112. After ringed stent elements 104 are properly positioned along inner graft element 108, inner graft element 108 and outer graft element 112 are bonded together. For example, heat may be applied to bond inner graft element 108 and outer graft element 112 together, thereby maintaining the position of ringed stent elements 104 with respect to graft member 114.

A first ringed stent element 106a includes a first apex 120a and a second ringed stent element 106b includes a second apex 120b. First apex 120a and second apex 120b may be adjacent to each other. For example, first ringed stent element 106a and second ringed stent element 106b may be oriented with respect to each other such that first apex 120a and second apex 120b are in a common plane 190 orthogonal to a longitudinal axis 192. Stated another way, first apex 120a and second apex 120b are in phase with each other. In other examples, first apex 120a and second apex 120b are not in a common plane orthogonal to longitudinal axis 192 (i.e., apices 120a and 120b are out of phase, or are otherwise not coplanar with each other). Although described with reference to specific examples, any orientation of ringed stent elements 104, including multiple different orientations with the same medical device (i.e., stent-graft) is within the scope of the present disclosure.

Stent-graft 100 may be delivered to and deployed within a treatment area of a patient. For example, with initial reference to FIGS. 2A and 2B, stent-graft 100 may be prepared and mounted to a catheter assembly 260 comprising a catheter tube 262 with a continuous lumen 264. A cover 266 can coaxially surround a balloon 268, which can be coupled to catheter tube 262 (as shown in FIG. 2B) and continuous lumen 264 at or near the distal end of catheter tube 262. Attachment of cover 266 to catheter tube 262 may be accomplished in various ways, including adhering the proximal and distal ends of cover 266 to catheter tube 262 using an adhesive, such as, for example, a cyanoacrylate adhesive. Further, polymeric tape and/or film may be used to secure the proximal and distal ends of cover 266 to catheter tube 262.

Balloon 268 can include, for example a generally tubular shaped balloon capable of inflating within the vasculature of a patient upon pressurization. For example, a biocompatible fluid, (e.g., water or saline), may be introduced into catheter tube 262, pass through continuous lumen 264 and through an inflation port (not shown) in catheter tube 262 located at the interior of balloon 268, and pressurize balloon 268. As pressure to balloon 268 is increased, the diameter of balloon 268 is also increased.

Balloon 268 can include, for example, a non-compliant, generally inelastic balloon. In such examples, balloon 268 can include a material that is configured to allow balloon 268 to expand to a chosen diameter upon sufficient pressurization and remain at or near the chosen diameter under further pressurization until a burst pressure is reached, such as, for example, nylon, polyethylene, polyethylene terephthalate (PET), polycaprolactam, polyesters, polyethers, polyamides, polyurethanes, polyimides, ABS copolymers, polyester/poly-ether block copolymers, ionomer resins, liquid crystal polymers and rigid rod polymers.

In some examples, balloon 268 can include a compliant, relatively elastic balloon. In such examples, balloon 268 can include a material that is configured to allow balloon 268 to continuously increase in diameter as pressure to balloon 268 is increased, such as, for example polyurethanes, latex and elastomeric organosilicone polymers, such as, polysiloxanes. Compliant, relatively elastic balloons may be preferable for deployment around a curve, such as within a vasculature of a patient as elastic balloons may mitigate undesirable straightening force during deployment. However, as compared to non-compliant, generally inelastic balloons, compliant, relatively elastic balloons are more susceptible to uneven deployment that can create angles between elements of an endoprosthesis leading to axially compressive forces. In particular, use of compliant balloons with endoprosthesis having independent ringed stent elements, a configuration providing relatively low straightening force, may be particularly susceptible to foreshortening during deployment.

In yet other examples, balloon 268 includes a semi-compliant balloon. In such examples, balloon 268 behaves in a combination of compliant and non-compliant attributes. Although described in connection with compliant and non-compliant examples, any material or configuration that allows balloon 268 to inflate in a predictable manner within the body of a patient, including in a combination of compliant and non-compliant behavior, is within the scope of the present disclosure. Examples of balloons providing low straightening forces are disclosed in United States Patent Publication Number 2014/0276406, titled, "Conformable balloon devices and methods," the entire contents of which are incorporated by reference herein.

Figure 3:
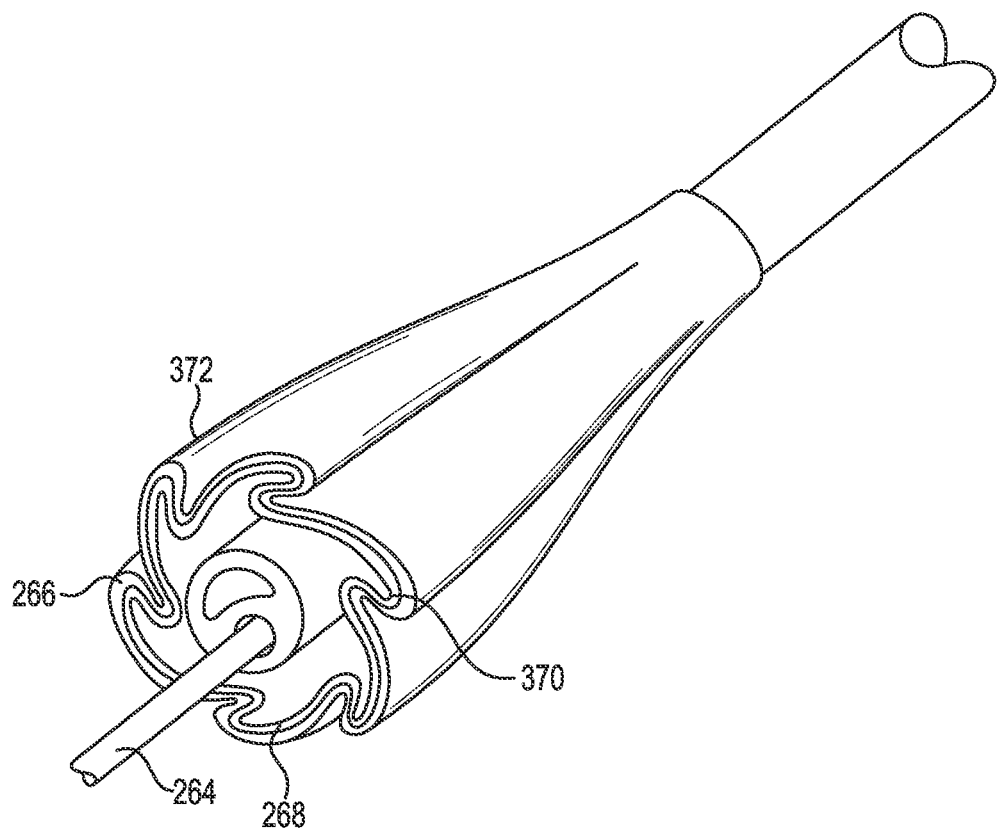
FIG. 3 illustrates a cutaway, perspective view of a medical device delivery system.

With reference to FIG. 3, balloon 268 and cover 266 may create an intermediate partial deployment diameter across a length of stent-graft 100 to reduce the maximum balloon angle during deployment to be no more than 35 degrees, such as no more than 20 degrees or even no more than 10 degrees. In some examples, balloon 268 and cover 266 are inflated by increasing an inflation pressure within balloon 268 until reaching an intermediate diameter between an undeployed diameter and a deployed diameter for an endoprosthesis mounted over balloon 268 and cover 266. The intermediate diameter may be approximately maintained at about the intermediate diameter until the inflation pressure increases to overcome a yield strength of cover 266. Such examples may be particularly useful with compliant, relatively elastic balloons, endoprosthesis having independent ringed stent elements and/or relatively large diameter endoprosthesis.

In one variation, cover 266 may include a frangible layer designed to rupture at the intermediate diameter with the ultimate strength of the frangible layer contributing to the yield strength of cover 266 to resist expansion beyond the intermediate diameter prior to yielding. Once the frangible layer fractures due to increased inflation pressure, expansion of the balloon 268 and cover 266 can continue to the deployed diameter.

In another variation, cover 266 can include a pre-stretched layer configured to provide increased resistance to expansion due to the yield strength of the cover to resist expansion beyond the intermediate diameter. For example, the assembly of balloon 268 and cover 266 may be partially inflated to the intermediate diameter prior to mounting an endoprosthesis. Such partial inflation causes one or more layers of balloon 268 and cover 266 to yield and plastically deform prior to deployment of an endoprosthesis, thereby reducing resistance to expansion of balloon 268 and cover 266 up to the intermediate diameter deployment of the endoprosthesis. Once reaching the intermediate diameter, the one or more layers of balloon 268 and cover 266 would again need to yield to permit further expansion, thereby providing increased resistance to expansion at the intermediate diameter.

In another variation, a cover comprising a helical wrap, and in one embodiment the helically wrapped cover is reduced or necked down in diameter to orient fibrils or strength members in cover to be longitudinal, and can then be partially inflated to the intermediate diameter prior to mounting an endoprosthesis. Such partial inflation changes the helical wrap angle and orientation of fibrils or strength members in cover to be more circumferential, which in effect can change amount of inflation pressure required to expand further. In this way, a "step" or pause in an inflation curve is achieved at the intermediate diameter.

In some examples, balloon 268 can include a plurality of pleats 370. Pleats 370 can include, for example, folds or inflection points in the material of balloon 268 extending generally along at least a portion of longitudinal axis 192. In such examples, balloon 268 includes a generally tubular shape having one or more pleats 370.

In some examples, balloon 268 may be coaxially surrounded by cover 266. Cover 266 can include an inner surface that can substantially conform to an outer surface of balloon 268, such that both balloon 268 and cover 266 include substantially the same shape, including when balloon 268 is deflated. However, in other examples, cover 266 can include a different shape or configuration from balloon 268.

In some examples, cover 266 can include a plurality of pleats 372. Similarly to balloon 268, pleats 372 can include, for example, folds or inflection points in the material of cover 266 extending generally along at least a portion of the longitudinal axis. In such examples, cover 266 includes a generally tubular shape having two or more pleats 372. In some examples, cover 266 includes the same number of pleats 372 as balloon 268. Along at least a section of or the entire working length of balloon cover 266, the inner surface of balloon cover 266 interfaces with the outer surface of balloon 268 in both the pleated, collapsed configuration and the un-pleated, inflated configuration. In other words, and as shown in FIG. 3, the pleated portions of the cover 266 substantially correspond in their configurations to the corresponding pleated portions of the balloon 268, and the non-pleated portions of the cover 266 substantially correspond in their configurations to the corresponding non-pleated portions of the balloon 268.

Pleats 370 and 372 may be formed in cover 266 and balloon 268 simultaneously. For example, balloon 268 may be coaxially surrounded by cover 266, and pleats 370 and 372 can then be formed in both balloon 268 and cover 266, respectively.

In other examples, pleats 372 may be formed in cover 266 after pleats 370 are formed in balloon 268. For example, a pre-pleated balloon 268 may be coaxially surrounded by cover 266. In such examples, both cover 266 and pre-pleated balloon 268 may be inflated together to a working pressure, after which cover 266 and balloon 268 are subjected to a mechanical pleat forming process that can form, for example, the same number and configuration of pleats in cover 266 as in pre-pleated balloon 268. While forming pleats 372 in cover 266, both cover 266 and balloon 268 may be deflated and compacted for delivery into the body of a patient. Although described in specific examples, any manner of forming pleats in cover 266 is within the scope of the present disclosure.

In yet other examples, balloon 268 can include a plurality of pleats 370 and cover 266 can include no pleats 372. In such examples, pleats 370 may be formed in balloon 268, followed by cover 266 being placed coaxially around the outer surface of balloon 268.

In addition, while pleats 370 and pleats 372 are illustrated as being consistent at regular intervals, in other examples, either or both of pleats 370 and pleats 372 may be replaced with micropleats, in which the material is simply crushed without predetermined fold or pleat locations.

In some examples, balloon cover 266 and balloon 268 may be formed separately and have different folds or pleatings once assembled with cover 266 and balloon 268. Although described in connection with specific examples (i.e., balloon 268 and cover 266 both comprising pleats, or only balloon 268 or cover 266 comprising pleats), any configuration in which balloon 268 and/or cover 266 includes a plurality of pleats or no pleats is within the scope of the present disclosure.

Cover 266 can include, for example, a polymer such as, for example, expanded fluoropolymers, such as, expanded polytetrafluoroethylene (ePTFE), modified (e.g., densified) ePTFE, expanded copolymers of PTFE, expanded polyethylene, woven and non-woven fabrics or films, and the like. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 9,139,669 to Xu et al. The entire contents of each of these aforementioned patents is hereby incorporated by reference.

In some examples, the polymer can include a node and fibril microstructure. In some examples, the polymer may be highly fibrillated (i.e., a non-woven web of fused fibrils). Although described in connection with specific polymers, any material or configuration that allows cover 266 to inflate in a predictable manner within the body of a patient is within the scope of the present disclosure.

In some examples, cover 266 can include multiple layers of a polymeric material. For example, cover 266 can include a polymeric material continuously wrapped over a substrate or mandrel to form a generally tubular member. In some examples, cover 266 may be constructed with circumferential-, helical-, or axial-orientations of the polymeric material. In such examples, the polymeric material may be wrapped generally perpendicular to the longitudinal axis of the mandrel or substrate, i.e., circumferentially wrapped. In other examples, the material may be wrapped at an angle between greater than 0 degrees and less than 90 degrees relative to the longitudinal axis of the mandrel or substrate, i.e., helically wrapped. In yet other examples, the polymeric material may be wrapped generally parallel to the longitudinal axis of the mandrel or substrate, i.e., axially (or longitudinally) wrapped.

With reference to FIG. 2B, cover 266 can, for example, have a length 282 that is greater than a length 280 of balloon 268. In some examples, cover 266 is placed around balloon 268 such that a first cover end 270 and a second cover end 272 extend beyond a first balloon end 274 and second balloon end 276. In such examples, a segment 284 of the material of cover 266 positioned at first cover end 270 or second cover end 272 may be compressed along longitudinal axis 192 (i.e., axially compressed). For example, with reference to FIGS. 4A and 4B, segment 284 of the material of cover 266 may be axially compressed (e.g., scrunched) at first cover end 270 and a segment 286 may be axially compressed at second cover end 272.

Figure 4A:
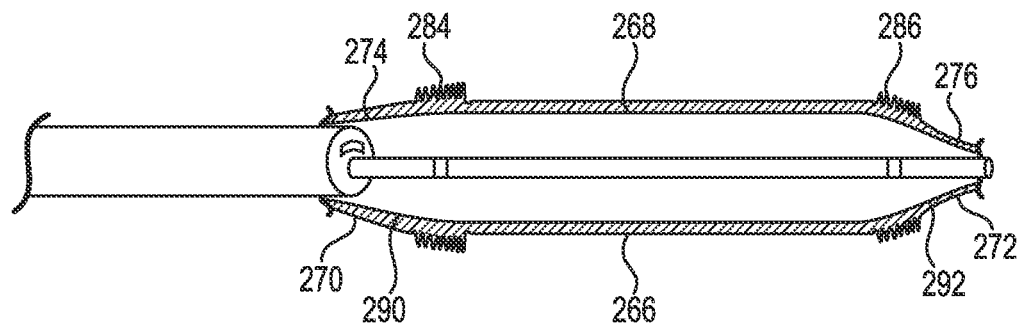
FIGS. 4A and 4B illustrate a cross sectional view of an undeployed balloon and cover and a cross sectional view of a deployed balloon, cover, and endoprosthesis, respectively.
Figure 4B:
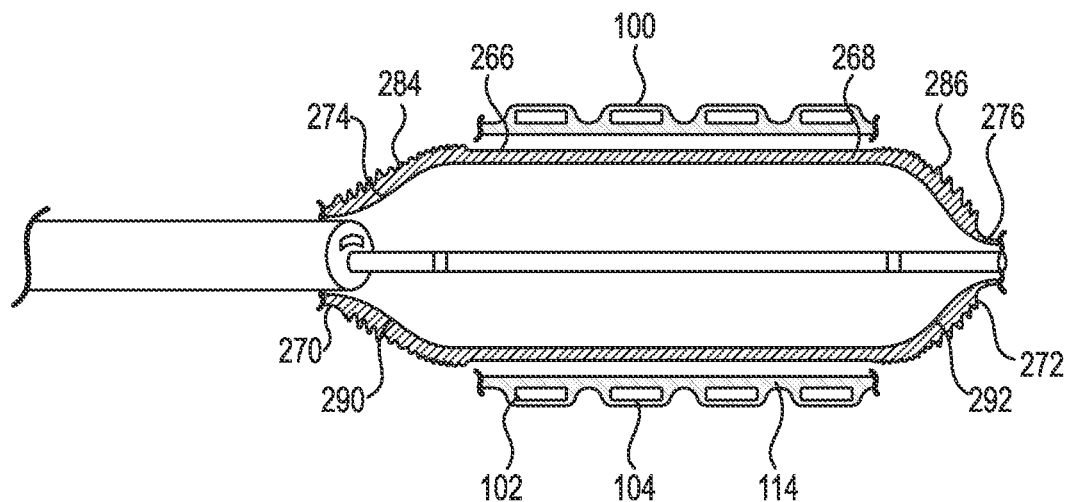

As shown in FIGS. 4A and 4B, segment 284 and/or segment 286 are aligned with a first balloon shoulder 290 and/or a second balloon shoulder 292. In other examples, the segments 284 and/or 286 are aligned with different portions of the balloon 268. In FIGS. 4A and 4B, the first balloon shoulder 290 and/or second balloon shoulder 292 are cone-shaped shoulders. Although described with reference to a specific example, any shape of balloon shoulder is within the scope of the present disclosure.

Segment 284 can, for example, be positioned such that it at surrounds at least a portion of first balloon shoulder 290, and segment 284 may be positioned such that it at surrounds at least a portion of second balloon shoulder 292. Providing additional axially compressed (e.g., scrunched) material around balloon shoulders (such as balloon shoulders 290 and 292) can increase the thickness and/or density of cover 266 in the general area of the balloon shoulders. Furthermore, having additional axially compressed material of the cover 266 over the balloon shoulders allows for radial expansion of balloon 268 while limiting axial compression to the balloon during inflation. For example, without having those compressed portions, the shoulders of the balloon will inflate before the body of the balloon and cause axial compression of the balloon and endoprosthesis. But with the axially compressed material, the shoulders of the balloon can expand in a manner that causes less axial compression of the endoprosthesis (e.g., due to the changed angle between the expanded portion of the balloon and the unexpanded or less expanded portion of the balloon) until the pressure within the balloon as a whole is sufficient to more fully expand the cover and the endoprosthesis surrounding the body of the balloon. Further, increased thickness and/or density in the general region of balloon shoulders 290 and 292 can provide additional radial strength to the balloon shoulders to achieve a similar effect.

As previously described above, the balloon 268 may be inflated by providing pressurized fluid into balloon 268. FIGS. 5A-5E illustrate one example of the cover 266 restricting expansion of balloon 268 to a predetermined intermediate diameter as the balloon 268 is inflated. The intermediate portion 200 of the stent-graft 100 imparts a resistance to expansion of the balloon 268 at the intermediate portion 20 of the stent-graft 100, as well as at, or proximate to, the free ends 196, 198. The cover 266 also imparts a resistance to expansion of the balloon to reduce a difference in an expansion rate of the balloon 268 at the free ends 196, 198 of the stent-graft 100 relative to an expansion rate of the balloon 268 at the intermediate portion 200 of the stent-graft 100 so as to reduce longitudinal compression of the stent-graft 100 as the balloon 268 expands the stent-graft 100 from its undeployed state (FIG. 5A) to its deployed state (FIG. 5E). In some examples, the cover 266 acts to equalize the expansion rate of the balloon 268 at the intermediate portion 200 of the stent with the expansion rate of the balloon at, or proximate to the free ends 196, 198 (e.g., proximate or at the shoulders).

In some examples, axially compressed segments 284 and/or 286 are configured to provide additional resistance to the expansion of balloon shoulders 290 and 292, causing a middle portion 294 of balloon 268 to inflate more readily than it would without such segments 284 and 286, which limits the expansion of the balloon shoulders to more closely match the expansion of the middle portion 294 of the balloon 268. Axially compressed segments 284 and/or 286 can also substantially impede inflation of balloon shoulder 290 and/or 292. In some examples, this has the effect of controlling the extent of balloon inflation in these regions which, in turn, controls the expansion profile of balloon 268 and/or stent-graft 100.

In some examples, the expansion of balloon 268 may be controlled by covered segments 284 and/or 286 in a manner that may reduce undesirable expansion characteristics of stent-graft 100. For example, covered segments 284 and/or 286 may reduce the degree of foreshortening of stent-graft 100 during expansion. In particular, segments 284 and/or 286 may be configured to force the balloon to into a specific inflation profile in which axial forces resulting from inflating balloon shoulders are significantly reduced, for example, due to the diminished angle between the shoulder portions of the balloon and the middle portion of the balloon or the stent-graft. Further, covered segments 284 and/or 286 may reduce or prevent stacking (e.g., reduction of spacing between ringed stent elements 104 during expansion) of stent-graft 100.

Figure 2A:
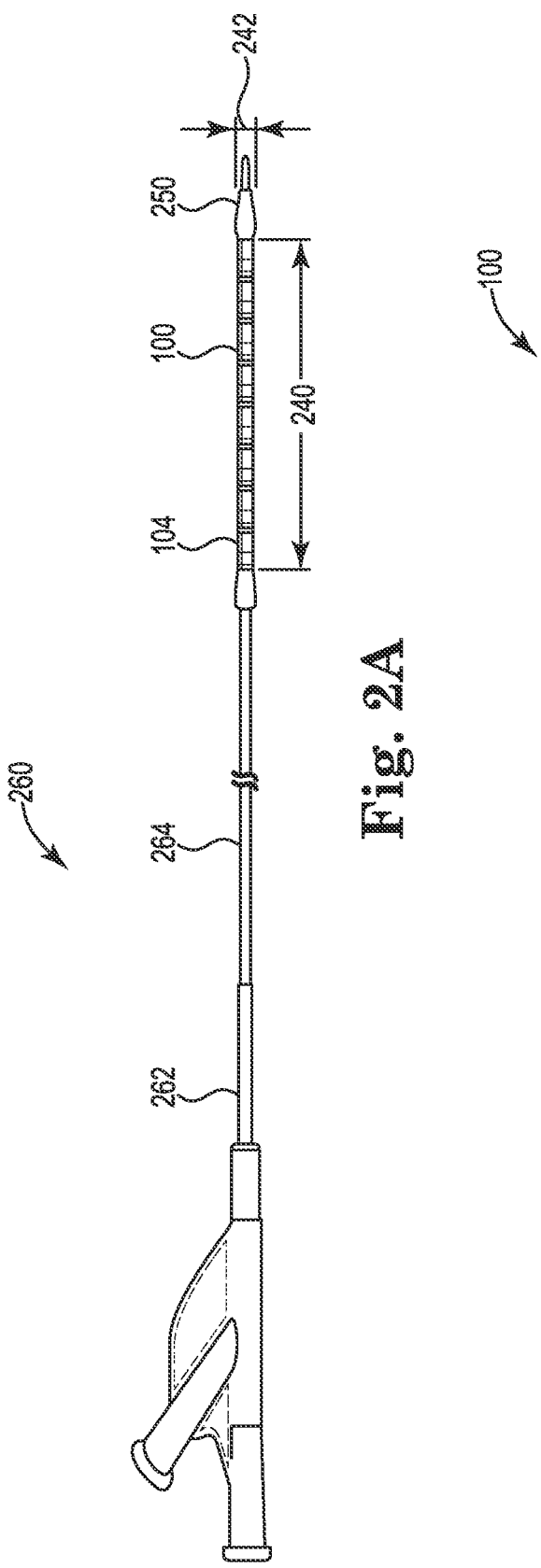
FIGS. 2A and 2B illustrate a side view and a partial cross section of an endoprosthesis delivery system.
Figure 2B:
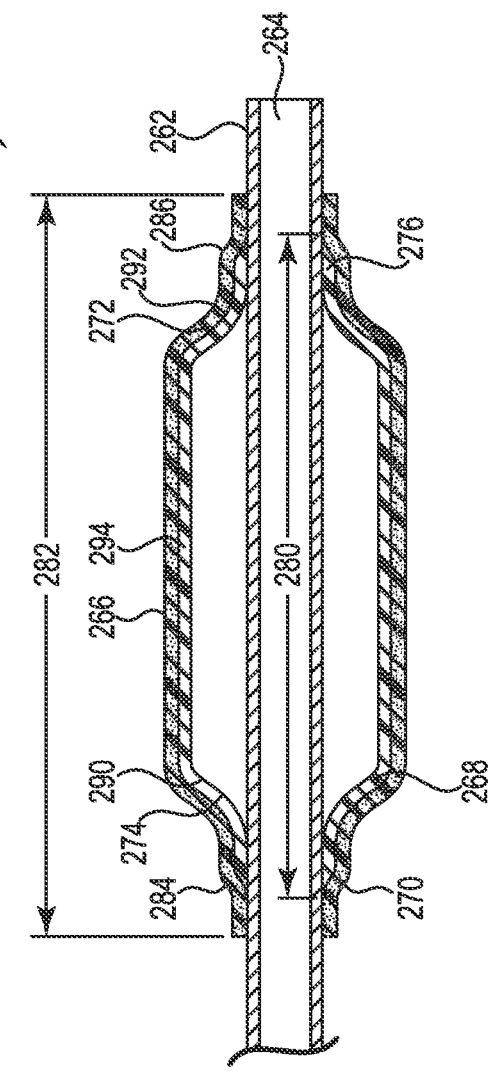

With reference to FIGS. 2A and 2B, after balloon 268 is surrounded by cover 266, stent-graft 100 may be loaded on to balloon 268 and cover 266. For example, stent-graft 100 may be positioned to concentrically surround a portion of balloon 268 and cover 266. In some examples, once stent-graft 100 is properly positioned around balloon 268 and cover 266, stent-graft 100 is radially compressed to an undeployed diameter 242. For example, stent-graft 100 may be compacted to undeployed diameter 242 to reduce the profile of stent-graft 100 during implantation within a treatment area. Further, stent-graft 100 may be compacted onto balloon 268 and cover 266 so as to resist movement of the stent-graft on balloon 268 prior to deployment. Following compaction, a profile of the medical assembly as measured about stent-graft 100 in the undeployed state may be between about 5 to about 10 French, with a thickness of cover 266 being between about 0.025 to about 0.051 millimeters.

In some examples, upon compaction, stent-graft 100 can imbed itself into cover 266. For example, by imbedding itself into cover 266, stent-graft 100 may exhibit improved stent retention. Such improved stent retention may, for example, assist in maintaining proper positioning of stent-graft 100 relative to cover 266 and/or balloon 268 during deployment to the treatment area of a patient.

Another way to limit any reduction in the length of the endoprosthesis (e.g., as measured between one free end 196 and the opposite free end 198) between its compressed and expanded configurations is by altering the position and/or orientation of the ringed stent elements 104 of a stent member 102. In particular, in some examples the position and/or orientation of one or more ringed stent elements 104 of stent member 102 may be altered prior to compaction of stent-graft 100. For example, the distance between two or more adjacent ringed stent element 104 may be reduced prior to compaction of stent-graft 100. For more particular examples, one or more ringed stent elements 104 may be moved so that they are each less than about 1 millimeters apart from each other or even so that they are in contact with one another (i.e., spaced 0 millimeters apart from each other).

In other examples, the position and/or orientation of ringed stent elements 104 may be altered after compaction of the stent-graft 100. For example, and with reference to FIG. 2A, stent-graft 100 has a length that may be changed by reducing the longitudinal spacing of two or more ringed stent element 104. Reducing the longitudinal spacing between adjacent ringed stent element 104 can, for example, create stored longitudinal length that is recovered when the stent element 104 is expanded into its deployed state. For example, stored longitudinal length may be defined as the length or segment of graft material of intra-ring graft segments 122 axially compressed between adjacent ringed stent elements 104 which is retrieved (i.e., axially expanded) upon expansion and deployment of stent-graft 100. The "undeployed length" of the stent-graft 100 generally refers to the stent-graft 100 in the compressed state prior to delivery and the "deployed length" of the stent-graft 100 generally refers to the stent-graft 100 in the expanded state. In some examples, changing the spacing of the ringed stent elements 104 creates a new length that may be referred to as the undeployed length (e.g., length 240 in FIG. 2A).

Stated another way, reducing the spacing between adjacent stent elements 104 can axially compress or scrunch intra-ring graft segments 122. By creating stored length by axial compression, the outside diameter of the stent-graft 100 is not increased. By not increasing the diameter of the device while creating stored length, the transverse-cross section of the device remains minimal and thus does not adversely affect delivery of the stent-graft through the vasculature. At the same time, recovery of the stored length increases the ability of the stent-graft to reduce or offset any loss of length, e.g., due to axial compression forces from inflating the balloon.

Upon delivery of stent-graft 100 to the treatment area of a patient, stent-graft 100 may be deployed. In some examples, stent-graft 100 is deployed by inflating balloon 268 to a desired diameter, thereby increasing the diameter of stent-graft 100 from an undeployed diameter 242 to a deployed diameter 146. After balloon 268 is sufficiently inflated, so that deployed diameter 146 is achieved, balloon 268 may be deflated, allowing for removal of catheter assembly 260 from the body of the patient.

Deployed length 148 can, for example, be less than undeployed length 240. For example, deployed length 148 may be about 60% to about 100% of undeployed length 240, and further, about 80% to about 100% and further, about 95% to about 100% of undeployed length 240. Testing has shown that certain examples have achieved deployed lengths 148 greater than 99% the undeployed length, thus demonstrating a foreshortening length of less than 1%. The ability of a stent-graft to achieve a high percentage of its undeployed length is also referred to herein as longitudinal efficiency.

Expanding stent-graft 100 from the undeployed configuration to the deployed configuration can also, for example, increase an internal angle of one or more wire frames 106 of ringed stent elements 104. For example, when stent-graft 100 is in the deployed configuration, internal angle 188 of wire frames 106 of ringed stent elements 104 may be between about 70 and 110 degrees, and further, between about 80 and 100 degrees.

As discussed above, expansion of stent-graft 100 may include inflating balloon 268 to a desired diameter, thereby increasing the diameter of stent-graft 100 from an undeployed diameter 242 to a deployed diameter 146. As shown in FIGS. 5A-5E, an angle along the outer surface of stent-graft 100 exists relative to the central longitudinal axis of stent-graft 100 between partially inflated portions of stent-graft 100 and fully inflated portions of stent-graft 100. For stent-grafts of relatively larger diameters, this angle may result in reduction of spacing between ringed stent elements 104 during expansion due to individual ringed stent elements 104 sliding longitudinally towards the center of stent-graft 100 while resisting expansion forces of balloon 268. For example, stent-grafts having diameters of about 10 millimeters or greater may experience reduction of spacing between ringed stent elements 104 during expansion.

In some examples, the balloon inflation profile can be controlled through the use of a cover over a balloon. There are several ways that such a cover could change the inflation profile so as to reduce the differences in balloon diameters across the longitudinal dimension of a stent-graft during expansion. Adding a cover to a balloon provides the ability to achieve a constant diameter over a range of inflation pressures. To maintain bending flexibility of the stent-graft during deployment, a cover may be able to lengthening on one side of a bend and/or shortening on the other side. A cover with the ability to lengthening and/or shorten when placed in a bend located on a balloon, such as an elastomeric balloon may provide a controlled inflation profile, and thereby limit balloon angle during deployment to mitigate axially compression of a stent graft while maintaining bending flexibility.

In some examples, the angles along an outer surface of stent-graft may be limited by controlling the inflation of the balloon to balance the inflation across the longitudinal dimension of the stent-graft during deployment. For example, a layer within or over the balloon, such a cover over the balloon, may counteract variable resistance of the stent to expansion of the balloon to mitigate uneven expansion of a stent-graft during the transition from the undeployed diameter to the deployed diameter. Such layers may combine with axially compressed sections of a balloon to counteract variable resistance of the stent to expansion of the balloon to mitigate uneven expansion of the stent. For example, such axially compressed sections of a balloon are described above with reference to FIGS. 4A and 4B in that segment 284 of the material of cover 266 may be axially compressed (e.g., scrunched) at first cover end 270 and a segment 286 may be axially compressed at second cover end 272.

A layer within or over the balloon may counteract variable resistance of the stent to expansion of the balloon to mitigate uneven expansion of a stent-graft by providing increased resistance to balloon deployment at weaker portions of the stent. In this manner, it is not required that such a layer extend across the entire longitudinal dimension of the balloon or across the entire longitudinal dimension of the stent-graft. Instead, a layer within or over the balloon configured to counteract variable resistance of the stent to expansion of the balloon to mitigate uneven expansion of the stent may be absent or minimal along one or more longitudinal sections in which expansion of the stent-graft offers more resistance than other longitudinal sections of the stent-graft. For example, the layer may be located at uncovered ends of the balloon, and optionally at weaker portions of the stent-graft including the ends of the sent graft and/or spaces between individual ringed stent elements.

In the same of different examples, a layer within or over the balloon configured to counteract variable resistance of the stent to expansion of the balloon to mitigate uneven expansion of the stent during the transition from the undeployed diameter to the deployed diameter may provide an increased resistance to expansion at a partially deployed balloon diameter. For example, such layers may provide a constraint layer designed to pause expansion of a balloon until pressure within the balloon is sufficient to overcome the strength of the frangible layer. Such pressures can limit angles between longitudinal portions of a balloon and may ensure all longitudinal portions of a balloon reach a partially-inflated state before any longitudinal portion of a balloon reaches a fully-inflated state.

In some examples, a balloon and a cover or portions thereof are inflated by increasing an inflation pressure within the balloon until reaching an intermediate diameter between an undeployed diameter and a deployed diameter, and approximately maintained at about the intermediate diameter until the inflation pressure increases to overcome a yield strength of the cover. In one variation, the cover may include a frangible layer designed to rupture at the intermediate diameter with the ultimate strength of the frangible layer contributing to the yield strength of cover to resist expansion beyond the intermediate diameter prior to yielding. Once the frangible layer fractures due to increased inflation pressure, expansion of the balloon and the cover can continue to the deployed diameter. In another variation, the cover can include a pre-stretched layer configured to provide increased resistance to expansion due to the yield strength of the cover to resist expansion beyond the intermediate diameter. In either example, the angle of ringed stent elements may be limited to mitigate foreshortening during deployment. In some examples, the angle of ringed stent elements may be limited to be no more than 35 degrees, such as no more than 20 degrees or even no more than 10 degrees.

In general, nylon (or other polymeric) balloons have little bending flexibility, but are capable of achieving a nearly constant diameter over a broad range of inflation pressures during differences in balloon diameters across the longitudinal dimension of a stent-graft during expansion. On the other hand, elastomeric balloons have a high degree of bending flexibility, but may result in high balloon angles over a range of inflation pressures if not constrained during expansion. Including a cover with an elastomeric balloon may mitigate differences in diameter over a range of inflation pressures may mitigate differences in balloon diameters across the longitudinal dimension of a stent-graft during expansion over a broad range of inflation pressures.

Figure 8:
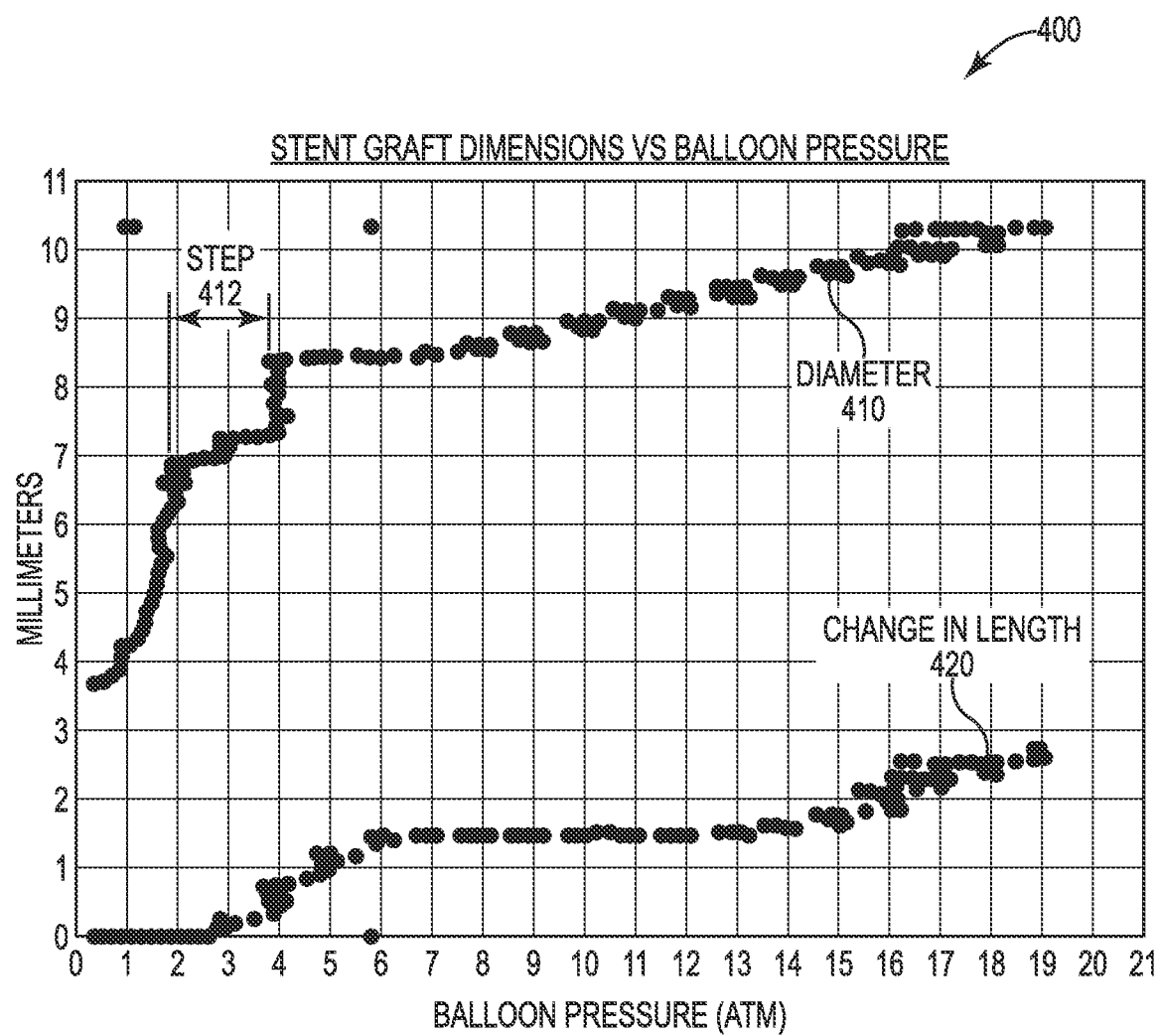
FIG. 8 is a chart illustrating diameter and length versus pressure during expansion of a endoprosthesis using a, endoprosthesis delivery system including a cover over a balloon configured to counteract variable resistance of an endoprosthesis to expansion of the balloon in accordance with in various stages of deployment.

As shown in FIG. 5A, balloon 268 and stent-graft 100 are in an undeployed state. In FIG. 5B, free ends 196, 198 of stent-graft 100 are partially inflated. As shown in FIG. 5C, intermediate portion 200 of stent-graft 100 begins to inflate, while free ends 196, 198 of stent-graft 100 are held at an intermediate diameter by cover 266. Expansion continues in this manner as shown in FIG. 5D. For example, the chart of FIG. 8 may represent dimensions of stent-graft 100 during deployment using assembly 260. As shown in FIG. 8, assembly 260 provides a pressure diameter curve 410 with step 412 where pressure increases while diameter stays relatively flat and an elongation curve 420 throughout its expansion range. Step 412 occurs prior to plastic deformation of cover 266, which then allows continued expansion past an intermediate diameter during deployment.

In this manner, cover 266 pauses expansion of balloon 268 for portions balloon 268 reaching the predetermined diameter of cover 266 until the pressure within balloon 268 overcomes the yield strength of cover 266, as shown in FIG. 5E. In this manner, cover 266 and balloon 268 portions of 266 and balloon 268 are inflated by increasing an inflation pressure within balloon 268 until reaching an intermediate diameter corresponding to a pre-stretched diameter of cover 266 and balloon 268.

The transition between FIG. 5D and FIG. 5E, corresponds to the step 412, in chart 400 of FIG. 8. For example, the balloon and the cover may inflated by increasing an inflation pressure within the balloon and approximately maintained at about the intermediate diameter until the inflation pressure increases by at least 1 atmosphere, such as increasing between about 1 and 12 atmospheres, between about 1 and 4 atmospheres or even increasing between about 1 and 2 atmospheres, to overcome a yield strength of the cover at least end portions of the balloon and cover. In some examples, the cover and balloon and optionally with an endoprosthesis, inflate up to intermediate diameter at relatively low pressures (e.g., 1, 2, 3, or 4 atmosphere) and then an additional pressure is required to expand past the intermediate diameter (e.g., 1, 2, 3, or 4 atmosphere) and then requiring an additional pressure to expand to deployed, or maximum intended, or fully expanded diameter (e.g., 3 to 18 atmosphere) (see FIG. 8 as one example).

The increase of pressure required to cause plastic deformation of a layer within cover 266 and balloon 268 may limit angles between different portions of balloon 268 and stent-graft 100 to be no more than 35 degrees, such as no more than 20 degrees or even no more than 10 degrees. In some examples, only portions of the balloon and the cover, such as end portions or portions except a middle portion that remains smaller, reach the intermediate diameter until the inflation pressure increases to overcome a yield strength of the cover. In other examples, substantially all portions of the balloon and the cover adjacent to the endoprosthesis such that each of the plurality of ringed stent elements approximately reach the intermediate diameter until the inflation pressure increases to overcome a yield strength of the cover.

Once pressure within the balloon is sufficient to overcome the yield strength, full expansion of balloon 268 and stent-graft 100 resumes, and continues until stent-graft 100 reaches its deployed state (FIG. 5E).

In one example, a balloon cover that pauses at an intermediate diameter (i.e. less than nominal diameter of balloon) was made by pre-stretching a film tube. A film having a bubble point of 20 psi, a thickness of 0.0003 inches, a mass of 2.66 grams/square meter, a matrix tensile strength of 94,933 psi, and an orthogonal matrix tensile strength of 2,407 psi, was helically wrapped on a mandrel having an approximate outside diameter of 11.6 mm (approximately 16% greater than nominal balloon), and baked at 380 degrees Centigrade for 15 minutes. The helically wrapped tube was then removed from the mandrel and necked down so the helically wrapped tube had an inside diameter of approximately 1.7 mm. The helically wrapped tube was then axially compressed ("scrunched") approximately 28% and then loaded onto a 10 mm balloon catheter. The helically wrapped tube ends were sealed to the balloon catheter and then the balloon catheter was inflated to 6 mm (a desired predetermined diameter). The balloon catheter with the pre-inflated helically wrapped tube was deflated and folded into a delivery diameter. The balloon catheter was then inflated and the balloon catheter had a "step" or pause in pressure vs diameter curve at or near the pre-inflated diameter of 6 mm, e.g., as shown in the example of FIG. 8.

Figure 6:
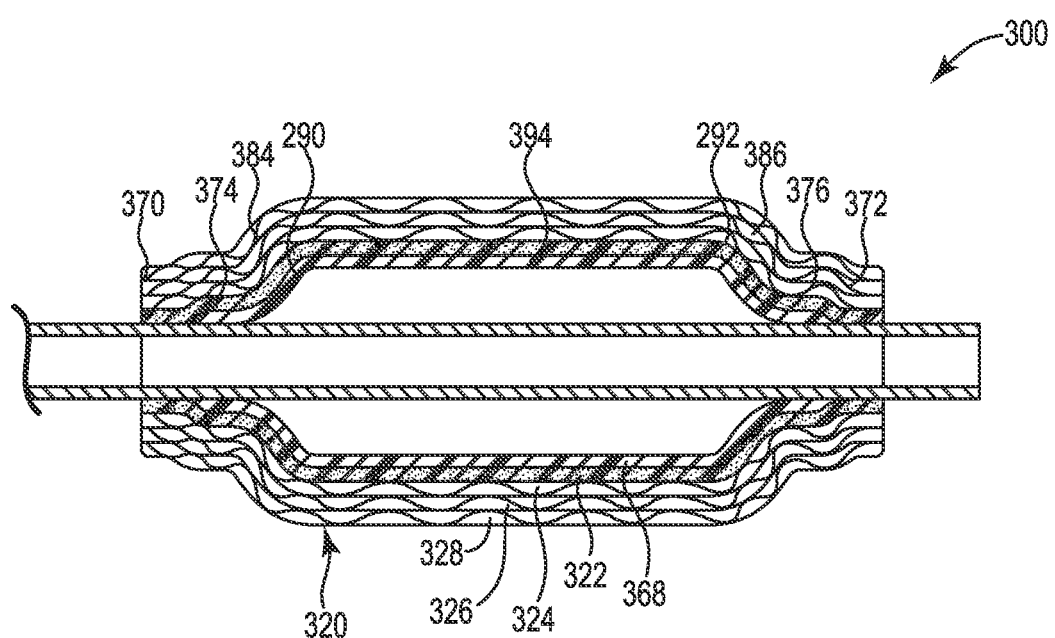
FIG. 6 illustrates a cross sectional views of a balloon and a cover over the balloon at various stages of expansion.

Another example of a balloon cover that pauses at an intermediate diameter is a balloon cover with a constraint layer as is illustrated in FIG. 6. FIG. 6 illustrates a longitudinal cross sectional view of assembly 300, which includes an deployed balloon 368 and a cover 320 with frangible layer 328. Frangible layer 328 is configured to counteract variable resistance of an endoprosthesis to expansion of balloon 368 by plastically deforming at pressures greater than those required to partially inflate balloon 368 along its entire length. In this manner, frangible layer 328 pauses expansion of balloon 368 for portions balloon 368 reaching the diameter of frangible layer 328, at which point pressure increases until pressure within the balloon is sufficient to overcome the strength of frangible layer 328, leading to plastic deformation (yield) of frangible layer 328. In some, but not all examples, such pressures may ensure all longitudinal portions of balloon 368 reach a partially-inflated state before any longitudinal portion of balloon 368 reaches a fully-inflated state. Such a partially-inflated state may not mean that all portions of balloon 368 are at the same diameter, but instead that differences in diameters are reduced, thereby reducing the angle between different longitudinal portions of balloon 368 to be no more than 35 degrees, such as no more than 20 degrees or even no more than 10 degrees, and thereby reducing axially compressive forces on a stent or stent-graft being deployed with balloon 368.

Cover 320 optionally includes more layers in addition to frangible layer 328. As shown in FIG. 6, cover 320 further includes three additional layers 322, 324, 326. In one example, layer 322 may represent a longitudinal wrap(s) of film, and layer 322 may provide longitudinal strength, which may serve to limit elongation of balloon 368 during inflation. Layer 322 may further comprise a coating (e.g., imbibed or an additional layer) of an adhesive (e.g., fluorinated ethylene propylene (FEP)). The FEP side of layer 322 may be facing abluminally or to outside of wrapped balloon. In one example, layer 322 is made from a base membrane as disclosed by U.S. Pat. No. 5,476,589 to Bacino, which is incorporated by reference herein, with an additional discontinuous layer of FEP on it as taught in as disclosed by PCT Pub. No. WO 94/13469 to Bacino, which is also incorporated by reference herein.

In the same or different examples, layer 324 may be added to cover 320 and represent one or more radial wraps of film over layer 322, such as a spiral wrapped layer(s), such as two to sixteen layers, such as eight layers, that may provide additional burst strength to cover 320. In some examples, layer 324 can also be made from a base membrane as disclosed by U.S. Pat. No. 5,476,589 to Bacino without FEP.

In the same or different examples, a layer 326 may be present in cover 320. Layer 326 may represent at least one spiral wrap of film over layer 324, such as one or more spiral wraps with FEP coated over layer 324. In one example, layer 326 is made from a base membrane as disclosed by U.S. Pat. No. 5,476,589 to Bacino, with an additional discontinuous layer of FEP on it as taught in as disclosed by PCT Pub. No. WO 94/13469 to Bacino.

In one particular example, layer 322 was made from a base membrane with discontinuous FEP that had a bubble point of 26 psi, the mass/area ~ 2.75 g/m^2 where ~0.5 g/m^2 of it is FEP, and had a force to break of 1.92 kgf/in in one direction and 0.06 Kgf/in in an orthogonal direction, and a thickness of 0.00013 inches. Layer 322 was wrapped on a 9 mm mandrel (intended to have an 8 mm endoprosthesis crushed onto cover over a balloon). In other examples, layer 322 may be wrapped directly on a balloon. In some examples, a balloon has a slightly larger (e.g., 1 mm or 2 mm) expanded diameter than the corresponding balloon cover or intended endoprosthesis. In this particular example, layer 324 was made by wrapping a film that had a bubble point of 20 psi, a thickness of 0.0003 inches, a mass of 2.66 grams/square meter, a matrix tensile strength of 94,933 psi, and an orthogonal matrix tensile strength of 2,407 psi, over layer 322. In this particular example, layer 326 was made from a base membrane with discontinuous FEP, that had a bubble point of 26 psi, the mass/area 2.75 g/m^2 where ~0.5 g/m^2 of it is from FEP, and had a force to break of 1.92 kgf/in in one direction and 0.06 Kgf/in in an orthogonal direction, and a thickness of 0.00013 inches, and wrapping over layer 324 (layer 326 was wrapped over layer 324). One skilled in the art may contemplate different layering scenarios and may combine individual layer properties into fewer layers, for various motivations such as profile or manufacturing benefits, and still be within scope of this disclosure.

Following the application of layers 322, 324, 326 over balloon 368, the assembly of balloon 368 and layers 322, 324, 326 may be cooked. In one example, the assembly of balloon 368 and layers 322, 324, 326 may be cooked at 320 degrees Celsius for a period of about 15 minutes. After this initial cooking, the assembly of balloon 368 and layers 322, 324, 326 may compressed to an intermediate diameter at 250 degrees Celsius.

Next, frangible layer 328 may be added to the assembly of balloon 368 and layers 322, 324, 326 at the intermediate diameter. In some examples, frangible layer 328 may represent at least one spiral wrap of film over layer 326, such as one or more spiral wraps with FEP coated over layer 326.

In one example, layer 328 is made from a base membrane as disclosed by U.S. Pat. No. 5,476,589 to Bacino, with an additional discontinuous layer of FEP on it as taught in as disclosed by PCT Pub. No. WO 94/13469 to Bacino. In one particular example, frangible layer 328 had a bubble point of 36 psi, a thickness of 0.00014 inches, a mass of 1.591 g/m^2 with 0.14 g/m^2 coming from FEP, force to break of 1.13 kg/in in one direction and 0.12 Kgf/in in an orthogonal direction.

In another example, layer 328 is made from a base membrane as disclosed by U.S. Pat. No. 5,476,589 to Bacino having an elastomer (Tecothane) imbibed into the base film where approximately 70% of total weight was from elastomer. The elastomer aided in cover retracting from endoprosthesis after deployment. The film without elastomer had a bubble point of approximately 35 psi, a thickness of 0.0001 inches, a mass of 1.46 g/m^2 and a matrix tensile strength in one direction of 101,321 psi and a matrix tensile strength in an orthogonal direction of 9,288 psi.

In the same or different examples, frangible layer 328 may be cooked to provide the frangible properties of frangible layer at the intermediate diameter. In one example, the assembly of balloon 368 and layers 322, 324, 326, 328 may be cooked at 280 degrees Celsius for a period of about 5 minutes. This process may produce a frangible layer 328 which experiences plastic deformation when pressure within balloon 368 reaches about four atmospheres. As best understood, the cooking melts and coalesces frangible layer 328 at the intermediate diameter, reducing the elasticity of frangible layer 328 and providing resistance to further inflation beyond the intermediate diameter. The cooked frangible layer 328 can be thin and discontinuous. During inflation with increasing inflation pressure, frangible layer 328 failing in tensile strain may cause the resumption of inflation past the intermediate diameter one frangible layer 328 fails in tensile strain, e.g., at about four atmospheres. As balloon 368 may inflate throughout its length at pressures less than the fracture point of frangible layer 328, frangible layer 328 may ensure that much or all of the length of balloon 368 may be partially inflated before frangible layer 328 experiences plastic deformation at any point along the length of balloon 368.

Following the cooking step, cover 320 and balloon 368 may be radially compressed to facilitate loading an endoprosthesis as discussed above with respect to FIGS. 2A and 2B. Following compaction, a profile of a medical assembly including an endoprosthesis, such as a stent or a stent-graft, loaded on as measured about stent-graft 100 in the undeployed state may be between about 5 to about 10 French, with a thickness of cover 320 being between about 0.025 to about 0.051 millimeters.

Except for the addition of frangible layer 328, cover 320 may be substantially similar to cover 266, and stent-graft may be may be loaded on to balloon 368 and cover 320 in the same or substantially similar manner to that described previously with respect to balloon 268 and cover 266. For example, construction of cover 320 can, for example, have a length 382 that is greater than a length 380 of balloon 368. In some examples, cover 320 is placed around balloon 368 such that a first cover end 370 and a second cover end 372 extend beyond a first balloon end 374 and second balloon end 376. In such examples, a segment 384 of the material of cover 320 positioned at first cover end 370 or second cover end 372 may be compressed along longitudinal axis 192 (i.e., axially compressed). For example, with reference to FIG. 6, segment 384 of the material of cover 320 may be axially compressed (e.g., scrunched) at first cover end 370 and a segment 386 may be axially compressed at second cover end 372. In the same or different examples, cover 320 may also be longitudinally compacted at other portions, such as middle portions or within spaced between ringed stent elements 104. In other examples, cover 320 may be compressed longitudinally along most or all of its length. In yet another alternative embodiment, the cover may not be compressed at all along its length.

As shown in FIG. 6, segment 384 and/or segment 386 are aligned with a first balloon shoulder 390 and/or a second balloon shoulder 392. In other examples, the segments 384 and/or 386 are aligned with different portions of the balloon 368. In FIG. 6, the first balloon shoulder 390 and/or second balloon shoulder 392 are cone-shaped shoulders. Although described with reference to a specific example, any shape of balloon shoulder is within the scope of the present disclosure.

Segment 384 can, for example, be positioned such that it at surrounds at least a portion of first balloon shoulder 390, and segment 384 may be positioned such that it at surrounds at least a portion of second balloon shoulder 392. Providing additional axially compressed (e.g., scrunched) material around balloon shoulders (such as balloon shoulders 390 and 392) can increase the thickness and/or density of cover 320 in the general area of the balloon shoulders. Furthermore, having additional axially compressed material of the cover 320 over the balloon shoulders allows for radial expansion of balloon 368 while limiting axial compression to the balloon during inflation. For example, without having those compressed portions, the shoulders of the balloon may more easily inflate before the body of the balloon and cause axial compression of the balloon and endoprosthesis. But with the axially compressed material, the shoulders of the balloon can expand in a manner that causes less axial compression of the endoprosthesis (e.g., due to the changed angle between the expanded portion of the balloon and the unexpanded or less expanded portion of the balloon) until the pressure within the balloon as a whole is sufficient to more fully expand the cover and the endoprosthesis surrounding the body of the balloon. Further, increased thickness and/or density in the general region of balloon shoulders 390 and 392 can provide additional radial strength to the balloon shoulders to achieve a similar effect.

As previously described above, the balloon 368 may be inflated by providing pressurized fluid into balloon 368. FIGS. 7A-7G illustrate one example of the cover 320 restricting expansion of balloon 368 to one desired inflation profile as the balloon 368 is inflated. For simplicity, with respect to FIGS. 7A-7G, reference numerals are shown only on FIG. 7A, although the same elements are also illustrated in FIGS. 7B-7G without reference numerals. FIG. 8 is a chart illustrating diameter and change length versus balloon pressure during expansion of a endoprosthesis using an endoprosthesis delivery system including a layer within or over a balloon configured to counteract variable resistance of an endoprosthesis to expansion of the balloon in accordance with in various stages of deployment.

Figure 7:
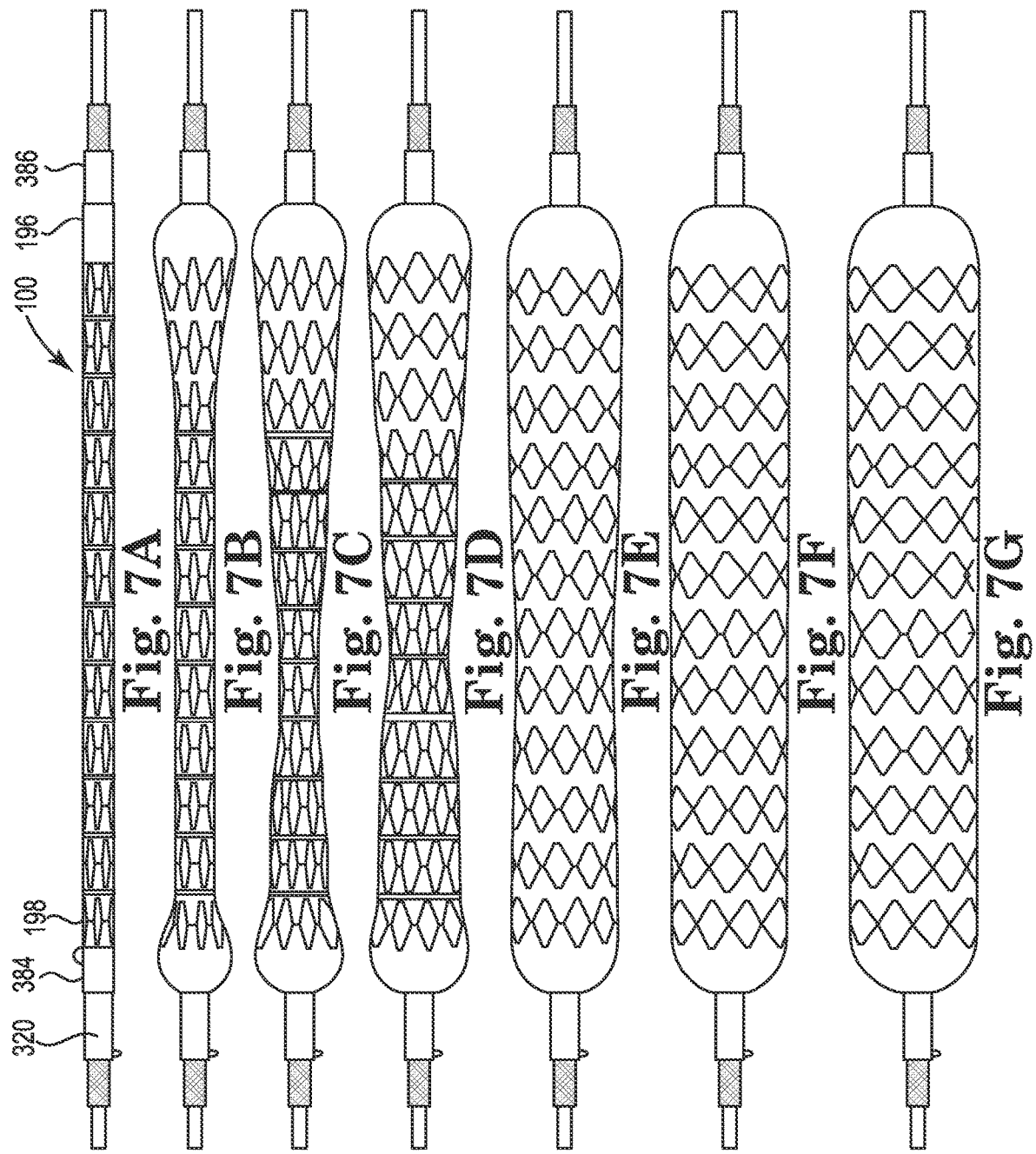
FIGS. 7A-7G illustrate side views of an endoprosthesis delivery system including a cover over a balloon configured to counteract variable resistance of an endoprosthesis to expansion of the balloon in accordance with in various stages of deployment.

The intermediate portion 200 of the stent-graft 100 imparts a resistance to expansion of the balloon 368 at the intermediate portion 30 of the stent-graft 100, as well as at, or proximate to, the free ends 196, 198. The cover 320 also imparts a resistance to expansion of the balloon to reduce a difference in an expansion rate of the balloon 368 at the free ends 196, 198 of the stent-graft 100 relative to an expansion rate of the balloon 368 at the intermediate portion 200 of the stent-graft 100 so as to reduce longitudinal compression of the stent-graft 100 as the balloon 368 expands the stent-graft 100 from its undeployed state (FIG. 7A) to its deployed state (FIG. 7G). Cover 320 also acts to equalize the expansion rate of the balloon 368 at the intermediate portion 200 of stent-graft 100 the expansion rate of the balloon at, or proximate to the free ends 196, 198 (e.g., proximate or at the shoulders).

As shown in FIG. 7A, balloon 368 and stent-graft 100 are in an undeployed state. In FIG. 7B, free ends 196, 198 of stent-graft 100 are partially inflated. As shown in FIG. 7C, intermediate portion 200 of stent-graft 100 begins to inflate, while free ends 196, 198 of stent-graft 100 are held at an intermediate diameter by frangible layer 328. Expansion continues in this manner as shown in FIG. 7D, where most of balloon and stent are at intermediate diameter. For example, the chart of FIG. 8 may represent dimensions of stent-graft 100 during deployment using assembly 300. As shown in FIG. 8, assembly 300 provides a pressure diameter curve 410 with step 412 where pressure increases while diameter stays relatively flat and an elongation curve 420 throughout its expansion range. Step 412 occurs prior to plastic deformation of frangible layer 328, which then allows continued expansion past an intermediate diameter during deployment.

In this manner, frangible layer 328 pauses expansion of balloon 368 for portions balloon 368 reaching the diameter of frangible layer 328 until the pressure within balloon 368 overcomes the yield strength of frangible layer 328, as shown in FIG. 7E. In this manner, balloon 368 and frangible layer 328, which may be a cover, exhibit an inflation profile in which frangible layer 328 and the ends of balloon 368 adjacent free ends 196, 198 of stent-graft 100 are inflated by increasing an inflation pressure within balloon 368 until reaching an intermediate diameter, between an undeployed diameter and a deployed diameter of stent-graft 100. The intermediate diameter is approximately maintained, with limited expansion, until the inflation pressure overcomes a yield strength, in this case the ultimate strength, of frangible layer 328. The transition between FIG. 7E and FIG. 7F, corresponds to the step 412, in chart 400 of FIG. 8. The increase of pressure required to cause plastic deformation of frangible layer 328 may ensure all longitudinal portions of balloon 368 reach a partially-inflated state before any longitudinal portion of balloon 368 reaches a fully-inflated state. Once all portions of balloon 368 reach the diameter of frangible layer 328, point pressure increases until pressure within the balloon is sufficient to overcome the strength of frangible layer 328, leading to plastic deformation of frangible layer 328. For example, the balloon and the cover may inflated by increasing an inflation pressure within the balloon and approximately maintained at about the intermediate diameter until the inflation pressure increases by at least 1 atmosphere, such as increasing between about 1 and 12 atmospheres, between about 1 and 4 atmospheres or even increasing between about 1 and 2 atmospheres, to overcome a yield strength of the cover at least end portions of the balloon and cover. In some examples, the cover and balloon and optionally with an endoprosthesis, inflate up to intermediate diameter at relatively low pressures (e.g., 1, 2, 3, or 4 atmosphere) and then an additional pressure is required to expand past the intermediate diameter (e.g., 1, 2, 3, or 4 atmosphere) and then requiring an additional pressure to expand to deployed, or maximum intended, or fully expanded diameter (e.g., 3 to 18 atmosphere) (see FIG. 8 as one example).

In some examples, only portions of the balloon and the cover, such as end portions or all portions except a middle portion, reach the intermediate diameter until the inflation pressure increases to overcome a yield strength of the cover. In other examples, substantially all portions of the balloon and the cover adjacent to the endoprosthesis such that each of the plurality of ringed stent elements approximately reach the intermediate diameter until the inflation pressure increases to overcome a yield strength of the cover.

In any event, full expansion of balloon 368 and stent-graft 100 resumes with increasing inflation pressure, as shown in FIG. 7F and continues until stent-graft 100 reaches its deployed state (FIG. 7G). As compared to the expansion profile of FIGS. 5A-5E, which is provided by a pre-stretched layer, frangible layer 328 may create a more consistent intermediate diameter about a length of stent-graft 100. However, both a pre-stretched layer and frangible layer represent suitable techniques for limiting angles between different longitudinal portions of a catheter assembly during deployment of a balloon expandable endoprosthesis to be no more than 35 degrees, such as no more than 20 degrees or even no more than 10 degrees, and thereby limiting foreshortening of the stent or stent graft.

In various examples, cover 320 may impart an elastic response near the fully deployed diameter of stent-graft 100 towards the intermediate diameter of FIG. 7E. In the same or different examples, cover 320 may include elements that impart an elastic response along the length of the stent at the fully deployed diameter towards the intermediate diameter, and such elements may be applied at the intermediate diameter, and/or such elements may be imbibed within cover 320. Elements that impart an elastic response towards the intermediate diameter may be stretched between the intermediate and fully deployed diameters, which may help with catheter removal and assist with release of stent-graft. In one example, a layer of Tecothane was added to frangible layer 328.

In some examples axially compressed segments 384 and/or 386 may also be configured to provide additional resistance to the expansion of balloon shoulders 390 and 392, causing a middle portion 394 of balloon 368 to inflate more readily than it would without such segments 384 and 386, which limits the expansion of the balloon shoulders to more closely match the expansion of the middle portion 394 of the balloon 368. Axially compressed segments 384 and/or 386 can also substantially impede inflation of balloon shoulder 390 and/or 392. In some examples, this has the effect of controlling the extent of balloon inflation in these regions which, in turn, controls the expansion profile of balloon 368 and/or stent-graft 100.

In some examples, the expansion of balloon 368 may be controlled by covered segments 384 and/or 386 in a manner that may reduce undesirable expansion characteristics of stent-graft 100. For example, covered segments 384 and/or 386 may reduce the degree of foreshortening of stent-graft 100 during expansion. In particular, segments 384 and/or 386 may be configured to force the balloon to into a specific inflation profile in which axial forces resulting from inflating balloon shoulders are significantly reduced, for example, due to the diminished angle between the shoulder portions of the balloon and the middle portion of the balloon or the stent-graft. Further, covered segments 384 and/or 386 may reduce or prevent stacking (e.g., reduction of spacing between ringed stent elements 104 during expansion) of stent-graft 100.

The techniques described with respect to assembly 300 may be particularly suitable for deployment of stent-grafts having diameters of at least 10 millimeters, such as, in various examples, diameters between about 11 millimeters to about 20 millimeters, between about 11 millimeters to about 16 millimeters, or between about 12 millimeters to about 13 millimeters.

Figure 9A:
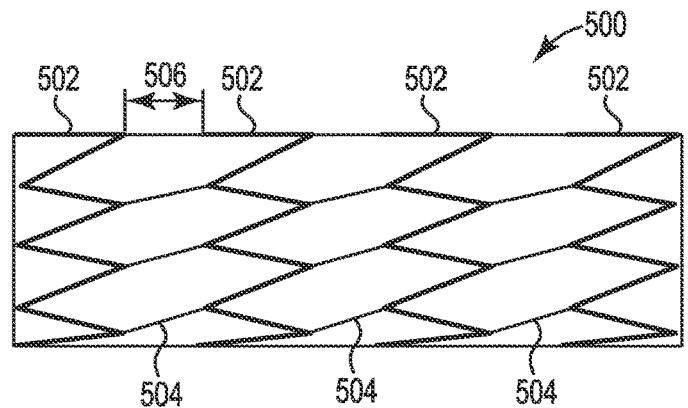
FIGS. 9A-9C illustrate side views of a stent.
Figure 9B:
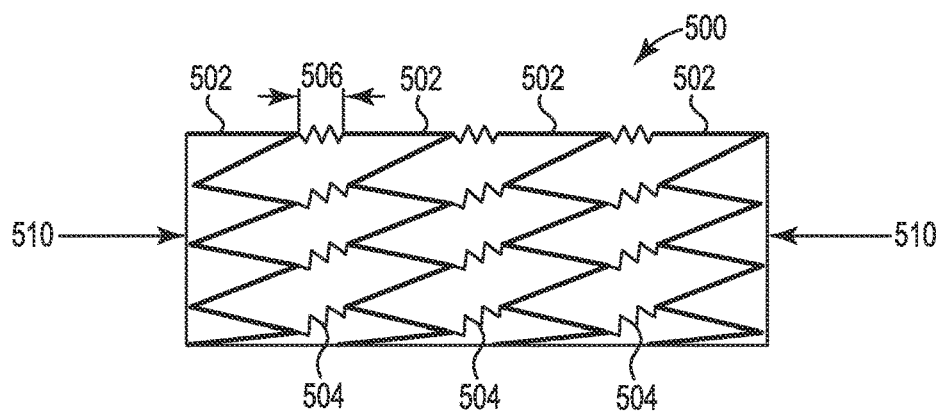
Figure 9C:
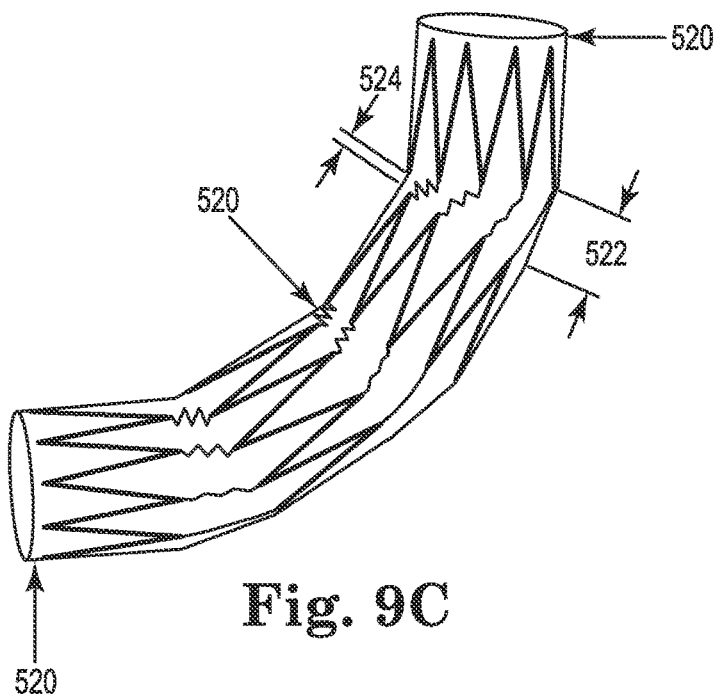

FIGS. 9A-9C illustrate stent 500. Stent 500 is one example of an endoprosthesis and includes ringed stent elements 502 and longitudinal stent elements 504 interconnecting ringed stent elements 502.

Stents, such as stent-graft 100, can be deployed on a balloon. The end elements of ringed stent elements 502 are not constrained by adjacent elements. Therefore, the end elements of ringed stent elements 502 deploy at a lower expansion force that the rest of the stent. With a simple deployment balloon having a consistent profile, during deployment, the end elements of ringed stent elements 502 will grow larger than the other elements of ringed stent elements 502. This creates an axially compressive force as the ringed stent elements 502 are pushed from the highest expansion portion of the balloon on the ends to the less expanded portion of the balloon towards the middle. The axial foreshortening force is a function of the angle of the balloon due to uneven expansion at the end element of ringed stent elements 502. The higher the angle, the greater the axially compressive force can be. The axial force from the balloon is resisted by the combination of the friction between the stent and the balloon and the bending strength of longitudinal stent elements 504. When the axial force from the balloon exceeds the bending strength of longitudinal stent elements 504, axial foreshortening will occur. As previously discussed, for larger stents, such as stents of 11 millimeters or greater, the angle may be enough to overcome frictional forces between the end elements of ringed stent elements 502 and the balloon, leading to axial foreshortening.

As previously disclosed herein, reducing the angle of the balloon due to uneven expansion mitigates axial foreshortening of stent 500 during deployment. In some examples, a cover on a balloon may create an intermediate partial deployment diameter across a length of stent 500 to reduce the maximum balloon angle during deployment. In some examples, a balloon and a cover or portions thereof are inflated by increasing an inflation pressure within the balloon until reaching an intermediate diameter between an undeployed diameter and a deployed diameter, and approximately maintained at about the intermediate diameter until the inflation pressure increases to overcome a yield strength of the cover.

The bending flexibility of stent 500 is determined in part by longitudinal stent elements 504. Longitudinal stent elements 504 can be rigid or can compress, fold or bend. Under bending load 520 (FIG. 9C), longitudinal stent elements 504 on the inside of the curve shorten, leaving gap 524 between adjacent ringed stent elements 502, and/or elements on the outside of the curve lengthen, leaving gap 522 between adjacent ringed stent elements 502.

In addition to affecting bending flexibility, longitudinal stent elements 504 affect column strength and forces required for axial foreshortening. In particular, longitudinal stent elements 504 resist longitudinal compression 510 (FIG. 9B), but once bending strength of longitudinal stent elements 504 is overcome, the spacing between adjacent ringed stent elements 502 shortens leaving gap 512 between adjacent ringed stent elements 502. As compared to stent-graft 100, which either includes no longitudinal stent elements or longitudinal stent elements with limited bending strength, the resistance of longitudinal stent elements 504 mitigates axial forces applied during deployment to reduce foreshortening.

In addition to limiting the angle of the balloon due to uneven expansion, another way to limit any reduction in the length of an endoprosthesis during deployment, such as stent 500, between its compressed and expanded configurations is by altering the position and/or orientation of the ringed stent elements 502. In particular, in some examples the position and/or orientation of one or more ringed stent elements 502 of stent 500 may be altered prior to compaction of stent 500. For example, the distance between two or more adjacent ringed stent element 502 may be reduced prior to compaction of stent 500. For more particular examples, one or more ringed stent elements 502 may be moved so that they are each less than about 1 millimeters apart from each other or even so that they are in contact with one another (i.e., spaced 0 millimeters apart from each other).

In other examples, the position and/or orientation of ringed stent elements 502 may be altered after compaction of the stent 500. For example, and with reference to FIG. 9B, stent 500 has a length that may be changed by reducing the longitudinal spacing of two or more ringed stent elements 502. Reducing the longitudinal spacing between adjacent ringed stent elements 502 can, for example, create stored longitudinal length that is recovered when the stent element 502 is expanded into its deployed state. For example, stored longitudinal length may be defined as the length or segment of longitudinal stent elements 504 axially compressed between adjacent ringed stent elements 502 which is retrieved (i.e., axially expanded) upon expansion and deployment of stent 500. The "undeployed length" of the stent 500 generally refers to the stent 500 in the compressed state prior to delivery and the "deployed length" of the stent 500 generally refers to the stent 500 in the expanded state. In some examples, changing the spacing of the ringed stent elements 502 creates a new length that may be referred to as the undeployed length.

Stated another way, reducing the spacing between adjacent stent elements 502 can axially compress longitudinal stent elements 504. By creating stored length by axial compression, the outside diameter of the stent 500 is not increased. By not increasing the diameter of the device while creating stored length, the transverse-cross section of the device remains minimal and thus does not adversely affect delivery of the stent-graft through the vasculature. At the same time, recovery of the stored length increases the ability of the stent-graft to reduce or offset any loss of length, e.g., due to axial compression forces from inflating the balloon.

While particular examples of the present invention have been illustrated and described herein, the present invention should not be limited to such illustrations and descriptions. It should be apparent that changes and modifications may be incorporated and embodied as part of the present invention within the scope of the following claims.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A delivery assembly comprising:
   an endoprosthesis;
   a catheter assembly onto which the endoprosthesis is received, the catheter assembly including, a balloon having a first end, a second end opposite the first end, a middle portion between the first end and the second end, the endoprosthesis received over the middle portion of the balloon, a first shoulder defined between the first end and a first side of the middle portion, and a second shoulder defined between the second end and a second side of the middle portion, the balloon being expandable from a delivery diameter to a deployed diameter and defining an intermediate diameter between the delivery diameter and the deployed diameter, and a cover assembly coaxially surrounding the balloon, the cover assembly formed of material defining a first segment positioned over at least a portion of the first shoulder and a second segment positioned over at least a portion of the second shoulder, the first and second segments impeding an expansion rate of the first shoulder and the second shoulder such that the expansion rate of the first shoulder and the second shoulder is more equalized with an expansion rate of the middle portion than would be exhibited by the first and second shoulders of the balloon in the absence of the cover assembly and such that a value of the intermediate diameter differs between the first end and the middle portion such that the intermediate diameter is greater at the first end than at the middle portion.

2. The delivery assembly of claim 1, wherein the balloon includes at least one of a compliant material, a semi-compliant material, and a non-compliant material.

3. The delivery assembly of claim 1, wherein a valve of the intermediate diameter of the second end is larger than the intermediate diameter of the middle portion.

4. The delivery assembly of claim 1, wherein the deployed diameter of the balloon is substantially equalized between the first end, the second end, and the middle portion after expansion.

5. The delivery assembly of claim 1, wherein the cover assembly further comprises a plurality of layers including an outer frangible layer designed to plastically deform when a yield strength of the frangible cover is overcome during expansion.

6. The delivery assembly of claim 5, wherein the cover assembly has at least two layers and up to sixteen layers.

7. The delivery assembly of claim 1, wherein the first shoulder and the second shoulder are cone-shaped.

8. The delivery assembly of claim 1, wherein the first segment and the second segment limit a tilt angle of the first end and second end relative to a longitudinal axis of the balloon during expansion.

9. The delivery assembly of claim 8, wherein the tilt angle is limited to less than 35 degrees.

10. The delivery assembly of claim 9, wherein a value of the tilt angle increases and decreases during expansion.

11. The delivery assembly of claim 10, wherein the value of the tilt angle is minimized at the deployed diameter.

12. The delivery assembly of claim 1, wherein the cover assembly is thicker at the first shoulder and the second shoulder than at the middle portion.

13. The delivery assembly of claim 1, wherein the first segment and the second segment have a scrunched configuration.

14. The delivery assembly of claim 1, wherein the endoprosthesis is positioned between the first and second segments.

15. The delivery assembly of claim 1, wherein the first and second segments are positioned along an outer surface of the cover assembly.

16. A delivery assembly comprising:

an endoprosthesis;

a catheter assembly onto which the endoprosthesis is received, the catheter assembly including, a balloon having a first end, a second end longitudinally opposite the first end, a middle portion between the first end and the second end onto which the endoprosthesis is mounted, a first shoulder defined between the first end and a first side of the middle portion, and a second shoulder defined between the second end and a second side of the middle portion, the balloon being expandable from a delivery diameter to a deployed diameter and defining an intermediate diameter between the delivery diameter and the deployed diameter, and a cover assembly coaxially surrounding the balloon, the cover assembly having a thickness at the first shoulder and the second shoulder that is larger than a thickness at the middle portion, the larger thickness at the first and second shoulders impeding an expansion rate of the first shoulder and the second shoulder, wherein the endoprosthesis is positioned between the first and second shoulders and increases a resistance to expansion of the middle portion such that the expansion rate of the first shoulder and the second shoulder is more equalized with an expansion rate of the middle portion as compared to the first and second shoulders in the absence of the cover assembly while at least one of the first and second ends inflates to the intermediate diameter more quickly than the middle portion.

17. The delivery assembly of claim 16, wherein the cover assembly includes a first segment having a first axially compressed material positioned over at least a portion of the first shoulder and a second segment having a second axially compressed material positioned over at least a portion of the second shoulder.

18. The delivery assembly of claim 16, wherein the increased thickness of the first and second shoulders is configured to limit axial compression of the balloon.

19. The delivery assembly of claim 16, wherein a value of the intermediate diameter of at least one of the first end of the balloon or the second end of the balloon is larger than a value of the intermediate diameter of in the middle portion during expansion.

20. The delivery assembly of claim 16, wherein the deployed diameter of the balloon is substantially equalized between the first end, the second end, and the middle portion after expansion.

* * * * *